(12) United States Patent
Kotowski et al.

(10) Patent No.: US 8,356,937 B2
(45) Date of Patent: Jan. 22, 2013

(54) ROTATABLE BOOM CARGO SCANNING SYSTEM

(75) Inventors: Andreas Kotowski, Rancho Palos Verdes, CA (US); Neeraj Agrawal, Rancho Palos Verdes, CA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 13/108,039

(22) Filed: May 16, 2011

(65) Prior Publication Data

US 2012/0121072 A1    May 17, 2012

Related U.S. Application Data

(63) Continuation of application No. 12/339,591, filed on Dec. 19, 2008, now Pat. No. 7,963,695, which is a continuation-in-part of application No. 11/948,814, filed on Nov. 30, 2007, now Pat. No. 7,517,149, which is a continuation of application No.

(Continued)

(51) Int. Cl.
*H05G 1/02* (2006.01)

(52) U.S. Cl. ........................................ 378/198

(58) Field of Classification Search ............... 378/198, 378/57, 62, 64, 187
See application file for complete search history.

(56) References Cited

U.S. PATENT DOCUMENTS

| | | |
|---|---|---|
| 2,831,123 A | 4/1958 | Daly |
| 3,766,387 A | 10/1973 | Heffan et al. |
| 3,784,837 A | 1/1974 | Holmstrom |
| RE28,544 E | 9/1975 | Stein et al. |
| 4,047,035 A | 9/1977 | Dennhoven et al. |
| 4,139,771 A | 2/1979 | Dennhoven et al. |
| 4,210,811 A | 7/1980 | Dennhoven et al. |
| 4,216,499 A | 8/1980 | Kunze et al. |
| 4,366,382 A | 12/1982 | Kotowski |
| 4,430,568 A | 2/1984 | Yoshida et al. |
| 4,566,113 A | 1/1986 | Donges et al. |
| 4,599,740 A | 7/1986 | Cable |
| 4,641,330 A | 2/1987 | Herwig et al. |
| 4,736,401 A | 4/1988 | Donges et al. |
| 4,788,704 A | 11/1988 | Donges et al. |
| 4,825,454 A | 4/1989 | Annis et al. |
| 4,884,289 A | 11/1989 | Glockmann et al. |
| 4,979,202 A | 12/1990 | Siczek et al. |
| 4,991,189 A | 2/1991 | Boomgaarden et al. |
| 5,022,062 A | 6/1991 | Annis |
| 5,065,418 A | 11/1991 | Bermbach et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,237,598 A | 8/1993 | Albert |

(Continued)

OTHER PUBLICATIONS

International Search Report for PCT/US2008/087654, Jul. 16, 2009, Rapiscan Security Products, Inc.

*Primary Examiner* — Irakli Kiknadze
(74) *Attorney, Agent, or Firm* — Novel IP

(57) ABSTRACT

The present application is a self-contained mobile inspection system and method and, more specifically, improved methods and systems for detecting materials concealed within a wide variety of receptacles and/or cargo containers. In particular, the present application is an improved method and system for inspecting receptacles and/or cargo containers using a single boom placed on a turntable with pivot points to allow for folding and unfolding of the boom, such that the inspection system is relatively compact in a stowed configuration and has a low center of gravity lending to greater stability.

20 Claims, 26 Drawing Sheets

Related U.S. Application Data

10/915,687, filed on Aug. 9, 2004, now Pat. No. 7,322,745, and a continuation-in-part of application No. 10/201,543, filed on Jul. 23, 2002, now Pat. No. 6,843,599, said application No. 12/339,591 is a continuation-in-part of application No. 12/051,910, filed on Mar. 20, 2008, now Pat. No. 7,519,148, which is a continuation of application No. 11/622,560, filed on Jan. 12, 2007, now Pat. No. 7,369,643, which is a continuation-in-part of application No. 10/915,687.

(60) Provisional application No. 60/493,935, filed on Aug. 8, 2003, provisional application No. 61/014,814, filed on Dec. 19, 2007.

U.S. PATENT DOCUMENTS

| Patent No. | Kind | Date | Inventor |
|---|---|---|---|
| 5,247,561 | A | 9/1993 | Kotowski |
| 5,253,283 | A | 10/1993 | Annis et al. |
| 5,313,511 | A | 5/1994 | Annis et al. |
| 5,367,552 | A | 11/1994 | Peschmann |
| 5,379,334 | A | 1/1995 | Zimmer et al. |
| 5,493,596 | A | 2/1996 | Annis |
| 5,638,420 | A | 6/1997 | Armistead |
| 5,642,393 | A | 6/1997 | Krug et al. |
| 5,642,394 | A | 6/1997 | Rothschild |
| 5,666,393 | A | 9/1997 | Annis |
| 5,687,210 | A | 11/1997 | Maitrejean et al. |
| 5,692,028 | A | 11/1997 | Geus et al. |
| 5,751,837 | A | 5/1998 | Watanabe et al. |
| 5,764,683 | A | 6/1998 | Swift et al. |
| 5,768,334 | A | 6/1998 | Maitrejean et al. |
| 5,787,145 | A | 7/1998 | Geus |
| 5,805,660 | A | 9/1998 | Perion et al. |
| 5,838,759 | A | 11/1998 | Armistead |
| 5,903,623 | A | 5/1999 | Swift et al. |
| 5,910,973 | A | 6/1999 | Grodzins |
| 5,930,326 | A | 7/1999 | Rothschild et al. |
| 5,940,468 | A | 8/1999 | Huang et al. |
| 5,974,111 | A | 10/1999 | Krug et al. |
| 6,031,890 | A | 2/2000 | Bermbach et al. |
| 6,058,158 | A | 5/2000 | Eiler |
| 6,067,344 | A | 5/2000 | Grodzins et al. |
| 6,081,580 | A | 6/2000 | Grodzins et al. |
| 6,094,472 | A | 7/2000 | Smith |
| 6,151,381 | A | 11/2000 | Grodzins et al. |
| 6,188,747 | B1 | 2/2001 | Geus et al. |
| 6,192,101 | B1 | 2/2001 | Grodzins |
| 6,192,104 | B1 | 2/2001 | Adams |
| 6,195,413 | B1 | 2/2001 | Geus et al. |
| 6,198,795 | B1 | 3/2001 | Naumann et al. |
| 6,218,943 | B1 | 4/2001 | Ellenbogen |
| 6,249,567 | B1 | 6/2001 | Rothschild et al. |
| 6,252,929 | B1 | 6/2001 | Swift et al. |
| 6,256,369 | B1 | 7/2001 | Lai |
| 6,278,115 | B1 | 8/2001 | Annis et al. |
| 6,282,260 | B1 | 8/2001 | Grodzins |
| 6,292,533 | B1 | 9/2001 | Swift et al. |
| 6,301,326 | B2 | 10/2001 | Bjorkholm |
| 6,320,933 | B1 | 11/2001 | Grodzins et al. |
| 6,356,620 | B1 | 3/2002 | Rothschild et al. |
| 6,424,695 | B1 | 7/2002 | Grodzins et al. |
| 6,434,219 | B1 | 8/2002 | Rothschild et al. |
| 6,435,715 | B1 | 8/2002 | Betz et al. |
| 6,442,233 | B1 | 8/2002 | Grodzins et al. |
| 6,445,765 | B1 | 9/2002 | Frank et al. |
| 6,453,003 | B1 | 9/2002 | Springer et al. |
| 6,453,007 | B2 | 9/2002 | Adams et al. |
| 6,456,684 | B1 | 9/2002 | Mun et al. |
| 6,459,761 | B1 | 10/2002 | Grodzins et al. |
| 6,459,764 | B1 | 10/2002 | Chalmers |
| 6,473,487 | B1 | 10/2002 | Le |
| RE37,899 | E | 11/2002 | Grodzins et al. |
| 6,483,894 | B2 | 11/2002 | Hartick et al. |
| 6,507,025 | B1 | 1/2003 | Verbinski et al. |
| 6,532,276 | B1 | 3/2003 | Hartick et al. |
| 6,542,574 | B2 | 4/2003 | Grodzins |
| 6,542,578 | B2 | 4/2003 | Ries et al. |
| 6,542,580 | B1 | 4/2003 | Carver et al. |
| 6,546,072 | B1 | 4/2003 | Chalmers |
| 6,552,346 | B2 | 4/2003 | Verbinski et al. |
| 6,563,903 | B2 | 5/2003 | Kang et al. |
| 6,580,778 | B2 | 6/2003 | Meder |
| 6,584,170 | B2 | 6/2003 | Aust et al. |
| 6,597,760 | B2 | 7/2003 | Beneke et al. |
| 6,606,516 | B2 | 8/2003 | Levine |
| 6,636,581 | B2 | 10/2003 | Sorenson |
| 6,653,588 | B1 | 11/2003 | Gillard-Hickman |
| 6,658,087 | B2 | 12/2003 | Chalmers et al. |
| 6,663,280 | B2 | 12/2003 | Doenges |
| 6,665,373 | B1 | 12/2003 | Kotowski et al. |
| 6,665,433 | B2 | 12/2003 | Roder |
| 6,763,635 | B1 | 7/2004 | Lowman |
| 6,785,357 | B2 | 8/2004 | Bernardi et al. |
| 6,812,426 | B1 | 11/2004 | Kotowski et al. |
| 6,816,571 | B2 | 11/2004 | Bijjani et al. |
| 6,837,422 | B1 | 1/2005 | Meder |
| 6,839,403 | B1 | 1/2005 | Kotowski et al. |
| 6,843,599 | B2 | 1/2005 | Le et al. |
| 6,920,197 | B2 | 7/2005 | Kang et al. |
| 7,039,159 | B2 | 5/2006 | Muenchau et al. |
| 7,207,713 | B2 | 4/2007 | Lowman |
| 2004/0141584 | A1 | 7/2004 | Bernardi et al. |
| 2005/0157842 | A1 | 7/2005 | Agrawal et al. |

ROTATABLE BOOM CARGO SCANNING SYSTEM

CROSS-REFERENCE TO RELATED APPLICATIONS

The present application is a continuation of U.S. patent application Ser. No. 12/339,591, filed on Dec. 19, 2008 now U.S. Pat. No. 7,963,695, which is:

- Is a continuation-in-part of U.S. patent application Ser. No. 11/948,814, entitled, "Single Boom Cargo Scanning System", filed on Nov. 30, 2007 now U.S. Pat. No. 7,517,149, which is a continuation of U.S. Pat. No. 7,322,745, entitled, "Single Boom Cargo Scanning System", filed on Aug. 9, 2004, which relies on, for priority, U.S. Provisional Patent Application No. 60/493,935, filed on Aug. 8, 2003 and is a continuation-in-part of U.S. patent application Ser. No. 10/201,543, entitled "Self-Contained Portable Inspection System and Method", filed on Jul. 23, 2002 and now U.S. Pat. No. 6,843,599;
- Is a continuation-in-part of U.S. patent application Ser. No. 12/051,910, entitled "Single Boom Cargo Scanning System", and filed on Mar. 20, 2008 now U.S. Pat. No. 7,519,148, which is a continuation of Ser. No. 11/622,560 U.S. Pat. No. 7,369,643, of the same title, filed on Jan. 12, 2007, which is a continuation-in-part of Ser. No. 10/915,687 filed Aug. 9, 2004 U.S. Pat. No. 7,322,745;
- Relies on U.S. Provisional Application No. 61/014,814, filed on Dec. 19, 2007, for priority;
- Is related to U.S. patent application Ser. No. 12/263,160, entitled "Cargo Scanning System", and filed on Oct. 31, 2008, which further relies on U.S. Provisional Patent Application No. 60/984,786, filed on Nov. 2, 2007, for priority, and is a continuation-in-part of U.S. Pat. No. 7,322,745; and
- Is related to U.S. patent application Ser. No. 10/939,986, entitled "Self-Contained Mobile Inspection System", and filed on Sep. 13, 2004, which further relies on U.S. Provisional Patent Application No. 60/502,498, filed on Sep. 12, 2003, for priority.

All of the above applications are herein incorporated by reference in their entirety.

FIELD OF THE INVENTION

The present application relates generally to a self-contained mobile inspection system and method and, more specifically, to improved methods and systems for detecting materials concealed within a wide variety of receptacles and/or cargo containers. In particular, the present application relates to improved methods and systems for inspecting receptacles and/or cargo containers using a single boom placed on a turntable with pivot points to allow for folding and unfolding of the boom, such that the inspection system is relatively compact in a stowed configuration and has a low center of gravity lending to greater stability.

BACKGROUND OF THE INVENTION

X-ray systems are used for medical, industrial and security inspection purposes because they can cost-effectively generate images of internal spaces not visible to the human eye. Materials exposed to X-ray radiation absorb differing amounts of X-ray radiation and, therefore, attenuate an X-ray beam to varying degrees, resulting in a transmitted level of radiation that is characteristic of the material. The attenuated radiation can be used to generate a useful depiction of the contents of the irradiated object. A typical single energy X-ray configuration used in security inspection equipment may have a fan-shaped or scanning X-ray beam that is transmitted through the object inspected. The absorption of X-rays is measured by detectors after the beam has passed through the object and an image is produced of its contents and presented to an operator.

Trade fraud, smuggling and terrorism have increased the need for such non-intrusive inspection systems in applications ranging from curbside inspection of parked vehicles to scanning in congested or high-traffic ports because transportation systems, which efficiently provide for the movement of commodities across borders, also provide opportunities for the inclusion of contraband items such as weapons, explosives, illicit drugs and precious metals. The term port, while generally accepted as referring to a seaport, also applies to a land border crossing or any port of entry.

With an increase in global commerce, port authorities require additional sea berths and associated container storage space. Additional space requirements are typically met by the introduction of higher container stacks, an expansion of ports along the coastline or by moving inland. However, these scenarios are not typically feasible. Space is generally in substantial demand and short supply. Existing ports operate under a routine that is not easily modified without causing disruption to the entire infrastructure of the port. The introduction of new procedures or technologies often requires a substantial change in existing port operating procedures in order to contribute to the port's throughput, efficiency and operability.

With limited space and a need to expand, finding suitable space to accommodate additional inspection facilities along the normal process route remains difficult. Additionally, selected locations are not necessarily permanent enough for port operators to commit to. Moreover, systems incorporating high-energy X-ray sources, or linear accelerators (LINAC), require either a major investment in shielding material (generally in the form of concrete formations or buildings) or the use of exclusion zones (dead space) around the building itself. In either case the building footprint is significant depending upon the size of cargo containers to be inspected.

A mobile inspection system offers an appropriate solution to the need for flexible, enhanced inspection capabilities. Because the system is relocatable and investing in a permanent building in which to accommodate the equipment is obviated, site allocation becomes less of an issue and introducing such a system becomes less disruptive. Also, a mobile X-ray system provides operators, via higher throughput, with the ability to inspect a larger array of cargo, shipments, vehicles, and other containers.

An example of a mobile X-ray inspection system is provided in U.S. Pat. No. 5,692,028 assigned to Heimann Systems. The '028 patent discloses an X-ray examining system comprising a mobile vehicle and an X-ray examining apparatus for ascertaining contents of an object, said apparatus including a supporting structure mounted on the mobile vehicle; said supporting structure being portal-shaped for surrounding the object on top and on opposite sides thereof during X-ray examination; said supporting structure including (i) a generally vertical column mounted on said vehicle and rotatable relative to said vehicle about a generally vertical axis; said column having an upper end; (ii) a generally horizontal beam having opposite first and second end portions; said beam being attached to said upper end at said first end portion for rotation with said column as a unit for assuming an inoperative position vertically above said mobile vehicle and an operative position in which said beam extends laterally from said vehicle; and (iii) an arm pivotally attached to said second end portion of said beam for assuming an inoperative position in which said arm extends parallel to said beam and an operative position in which said arm extends generally vertically downwardly from said beam; an X-ray source for generating a fan-shaped X-ray beam; said X-ray source being carried by said vehicle; and an X-ray detector mounted on said supporting structure; said X-ray examining system being adapted to travel along the object to be examined while irradiating the object and detecting the X-rays after passage thereof through the object.

U.S. Pat. No. 5,764,683 assigned to AS&E discloses a device for inspecting a cargo container, the device comprising: a bed moveable along a first direction having a horizontal component; a source of penetrating radiation, mounted on the bed, for providing a beam; a motorized drive for moving the bed in the first direction; at least one scatter detector mounted on the bed, the at least one scatter detector having a signal output; and a transmission detector for detection penetrating radiation transmitted through the cargo container such that the beam is caused to traverse the cargo container as the bed is moved and the at least one scatter detector and the transmission detector each provide a signal for characterizing the cargo container and any contents of the cargo container.

U.S. Pat. No. 6,252,929 assigned to AS&E claims a device for inspecting a cargo container with penetrating radiation, the device comprising: a bed that is reversibly moveable along a direction having a horizontal component; a source of penetrating radiation, mounted on the bed for providing a beam having a central axis, the central axis being predominantly horizontal; a motorized drive for moving the bed in the first direction; at least one scatter detector mounted on the bed, each scatter detector having a signal output; so that, as the bed is moved forward and backward along the direction, the beam is caused to traverse the cargo container as the bed is moved and each scatter detector provides a signal for characterizing the cargo container and any contents of the cargo container.

U.S. Pat. No. 6,292,533, also assigned to AS&E, claims a system for inspecting a large object with penetrating radiation during motion of the system in a scan direction, the system comprising: a vehicle having wheels and an engine for propelling the vehicle on highways; a boom having a proximal end rotatable about a point on the vehicle and a distal end, the boom deployed transversely to the scan direction for straddling the object during operation of the system; a source of penetrating radiation coupled to the vehicle for providing a beam so that the beam is caused to irradiate a first side of the object as the vehicle is moved in the scan direction; and at least one detector coupled to the vehicle on a side of the object opposing the first side, the at least one detector having a signal output, the at least one detector providing a signal for imaging the object.

U.S. Pat. No. 5,903,623, assigned to AS&E, claims a device, for inspecting a large object with penetrating radiation, the device comprising: a self-propelled vehicle capable of on-road travel; a source of penetrating radiation, mounted on the vehicle, for providing a beam of penetrating radiation; a beam stop for absorbing the beam of penetrating radiation after traversal of the object; and at least one detector coupled to the vehicle, the at least one detector having a signal output so that the beam is caused to traverse the object in a first direction as the vehicle is moved and the signal output characterizes the object.

In addition to the features described above, conventional relocatable inspection systems generally comprise at least two booms, wherein one boom will contain a plurality of detectors and the other boom will contain at least one X-ray source. The detectors and X-ray source work in unison to scan the cargo on the moving vehicle. In conventional single boom relocatable inspection systems, the X-ray source is located on a truck or flatbed and the detectors on a boom structure extending outward from the truck.

The aforementioned prior art patents are characterized by moving-scan-engine systems wherein the source-detector system moves with respect to a stationary object to be inspected. Also, the detectors and the source of radiation are either mounted on a moveable bed, boom or a vehicle such that they are integrally bound with the vehicle. This limits the flexibility of dismantling the entire system for optimum portability and adjustable deployment to accommodate a wide array of different sized cargo, shipments, vehicles, and other containers. As a result these systems can be complicated to deploy and pose several disadvantages and constraints.

For example, in a moving-scan-engine system the movement of the source and detector, relative to a stationary object, may cause lateral twist and lift and fall of the detector or source, due to movement of the scanner over uneven ground, inducing distortions in the scanned images and faster wear and tear of the scanner system. Systems where the weight of the detector or source is held on a boom require high structural strength for the boom in order to have the boom stable for imaging process, thereby adding more weight into the system. Such systems that require a detector-mounted boom to unfold during deployment may cause an unstable shift of the center of gravity of the system off the base, causing the system to tip over. Further, in the case of moving-scan-engine systems using a "swing arm" boom approach, the driver driving the scanner truck is unable to gauge the possibility of hitting the detector box, mounted on a boom, with a vehicle under inspection (VUI), as the detector box is on the other side of the VUI during scanning and not visible to the driver.

Additionally, with moving-scan-engine systems, the truck supporting the scanner system is always required to move the full weight of the scanner regardless of the size and load of the VUI, putting greater strain on the scanning system. Further, because of the integrated nature of prior art systems, swapping detector and radiation systems between scanning systems is not feasible. In terms of throughput, prior art systems need additional operational systems that greatly multiply the cost of operation to increase the number of VUI to be handled. Also disadvantageous in conventional systems is that they suffer from a lack of rigidity, are difficult to implement, and/or have smaller fields of vision.

Accordingly, there is need for improved inspection methods and systems built into a fully self-contained, over-the-road-legal vehicle that can be brought to a site and rapidly deployed for inspection. The improved method and system can, therefore, service multiple inspection sites and set up surprise inspections to thwart contraband traffickers who typically divert smuggling operations from border crossings that have tough interdiction measures to softer crossings with lesser inspection capabilities. Moreover, there is an additional need for methods and systems that require minimal footprint to perform inspection and that use a sufficient range of radiation energy spectrum to encompass safe and effective scanning of light commercial vehicles as well as substantially loaded 20-foot or 40-foot ISO cargo containers. It is important that such scanning is performed without comprising the integrity of the cargo and should ideally be readily deployable in a variety of environments ranging from airports to ports of entry where a single-sided inspection mode needs to be used due to congested environments. Such needs are addressed in U.S. Pat. No. 6,543,599, entitled "Self-Contained Portable Inspection System and Method", which is herein incorporated by reference in its entirety.

Improved methods and systems are additionally needed to keep the relative position between the radiation source and detector fixed to avoid distortion in images caused by the movement of scanner and/or detectors over uneven ground or due to unstable structures. Moreover, there is a need for improved methods and systems that can provide comprehensive cargo scanning in portable and stationary settings. Specifically, methods and systems are needed in which a single boom is employed for generating quality images for inspection. Further, the system should be mounted on a relocatable vehicle, capable of receiving and deploying the boom.

What is also needed is a single boom cargo scanning system that enables quick and easy deployment, rigidity and tight alignment of the radiation sources and detectors, and a narrow collimated radiation beam, thus allowing for a smaller exclusion zone. In addition, what is needed is an optimal scanning system design that allows for the radiation source to be closer to the Object under Inspection ("OUI"), thereby allowing for higher penetration capability and complete scanning of the target vehicle without corner cutoff. Such needs are addressed in the U.S. Pat. No. 7,322,745, entitled "Single Boom Cargo Scanning System" which is herein incorporated by reference in its entirety.

What is also needed is a system that can be stowed in a relatively compact area so that it can be transported on smaller and in particular, cargo aircraft. In addition, what is also needed is a scanning system which has a low center of gravity in a stowed position, thereby allowing for road transport in challenging, steep and hilly areas.

What is also needed is a scanning system that can be deployed from a stowed configuration to an operational configuration in operating areas having limited horizontal or vertical clearance.

SUMMARY OF THE INVENTION

The present application is directed to a self-contained mobile inspection system and method for detecting materials concealed within a wide variety of receptacles and/or cargo containers. In particular, the present application is directed to an improved method and system for inspecting receptacles and/or cargo containers using a single boom placed on a turntable with pivot points to allow for folding and unfolding of the boom, such that the inspection system is relatively compact in a stowed configuration and has a low center of gravity lending to greater stability.

In one embodiment, the present application is directed to a portable inspection system for generating an image representation of target objects using a radiation source, comprising: a foldable boom comprising a first vertical portion, a first horizontal portion, and a second vertical portion; a first detector array housing physically attached to the first horizontal portion of the foldable boom, wherein said first detector array housing contains a plurality of detectors; a second detector array housing physically attached to the first vertical portion of the foldable boom wherein the second detector array housing contains a plurality of detectors; at least one source of radiation, wherein said source of radiation is securely attached to a distal end of the second vertical portion of said boom; and a turntable, having a top portion physically attached to a proximal end of the first vertical portion of said boom and a bottom portion physically attached to a rig for rigidly securing the first vertical portion of the boom during transport and deployment.

Further, the radiation source comprises at least one gamma ray source, wherein in one embodiment, the at least one gamma ray source is $^{60}$Co and the $^{60}$Co source is substantially mono-energetic and capable of emitting photons at two distinct energy levels. In another embodiment, the at least one gamma ray source $^{137}$Cs.

In one embodiment, the radiation source and detector array are located on the same single foldable boom.

In one embodiment, the turntable is rotatable from 0 to 360 degrees and is used to select a scan angle position. In one embodiment, the scan angle position of the turntable, upon deployment of the system, ranges between 80° and 100°. In another embodiment, the scan angle position of the turntable, upon deployment of the system, ranges between 260° and 280°.

In yet another embodiment, the present application is directed to a portable inspection system for generating an image representation of target objects using a radiation source, comprising: a foldable boom comprising a first vertical portion, a first horizontal portion, and a second vertical portion; a first detector array housing physically attached to the first horizontal portion of the foldable boom, wherein said first detector array housing contains a plurality of detectors; a second detector array housing physically attached to the first vertical portion of the foldable boom wherein the second detector array housing contains a plurality of detectors; at least one source of radiation, wherein said source of radiation is securely attached to a distal end of the second vertical portion of said boom; and a turntable, having a top portion physically attached to a proximal end of the first vertical portion of said boom and a bottom portion physically attached to a rig for rigidly securing the first vertical portion of the boom during transport and deployment, wherein the system further comprises a small overall dimension in a stowed position to fit in cargo transport aircraft and a low center of gravity in a stowed position for facile movement on steep hills and uneven roadways.

In another embodiment, the invention comprises a portable inspection system for generating an image representation of target objects using a radiation source, comprising a foldable boom comprising a first section connected to a second section using a first connecting member; a second section connected to a third section, using a second connecting member, and a fourth section connected to a second section at the first connecting member; a first detector array housing physically attached to the second section of the foldable boom, wherein said first detector array housing contains a plurality of detectors; a second detector array housing physically attached to the fourth section of the foldable boom wherein the second detector array housing contains a plurality of detectors; at least one source of radiation, wherein said source of radiation is securely attached to a distal end of the third section of the boom; and a turntable, having a top portion physically attached to a proximal end of the first section the boom and a bottom portion physically attached to a rig for rigidly securing the first section the boom during transport and operation.

In another embodiment, the invention comprises a cargo inspection system comprising: a radiation source and a detector array housed in a foldable boom structure having at least two configurations: the first configuration comprises a) a first section in a first plane, physically connected, at its proximal end, to a turntable, wherein said first plane is substantially parallel to a surface platform on a vehicle; b) a second section, also in said first plane, wherein said second section is substantially parallel to the first section, and connected to said first section through a first connecting member; and c) a third section, also is said first plane, wherein said third section is substantially parallel to the first section and the second section, and connected to the second section through a second connecting member; and the second configuration comprises a) said first section, in a second plane, wherein said second plane is at a non-parallel angle to the surface platform on the vehicle; b) said second section, in said second plane, wherein said second section is substantially perpendicular to the first section, and connected to said first section through the first connecting member; and c) said third section, in said second plane, wherein said third section is substantially parallel to the first section and perpendicular to the second section and wherein said third section is connected to the second section through the second connecting member.

Optionally, the non-parallel angle is 45 degrees or 90 degrees. Optionally, a fourth section is perpendicular to the second section. Optionally, the radiation source comprises at least one gamma ray source. Optionally, the turntable is rotatable from 0 to 360 degrees and used to establish a scan angle position, such as between 80° and 100°. The detector array is located on at least one of the second section or fourth section.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following Detailed Description when considered in connection with the accompanying drawings, wherein.

DETAILED DESCRIPTION OF THE INVENTION

The present application is directed towards a portable inspection system for generating an image representation of target objects using a radiation source, comprising a mobile vehicle; a detector array physically attached to a single, movable boom having a proximal end and a distal end wherein the proximal end is physically attached to a turntable located on the mobile vehicle; and at least one source of radiation wherein the radiation source is fixedly attached to the distal end of the boom and adjustable to a desired scanning height. The image is generated by introducing target objects between the radiation source and the detector array, thereby exposing objects to radiation and subsequently detecting the radiation. The boom, which is fixedly attached to a turntable, can be rotated and unfolded from a first stowed configuration to a second deployed and operational configuration.

The system is advantageous, among other benefits, in that it provides a highly compact stowed configuration with low center of gravity for stability; a sturdy deployed configuration with radiation source and detectors readily aligned; a selectable scan angle position, and it can be converted from a stowed configuration to a deployed and operational configuration in areas having limited horizontal and vertical clearance. The inspection methods and systems of the present invention are mobile, rapidly deployable, and capable of scanning a wide variety of receptacles cost-effectively and accurately, with rigidity, ease of use, and a wider field of vision.

Various modifications to the preferred embodiment, disclosed herein, will be readily apparent to those of ordinary skill in the art and the disclosure set forth herein may be applicable to other embodiments and applications without departing from the spirit and scope of the present invention and the claims hereto appended. Reference will now be made in detail to specific embodiments of the invention. Language used in this specification should not be interpreted as a general disavowal of any one specific embodiment or used to limit the claims beyond the meaning of the terms used therein.

Figure 1:
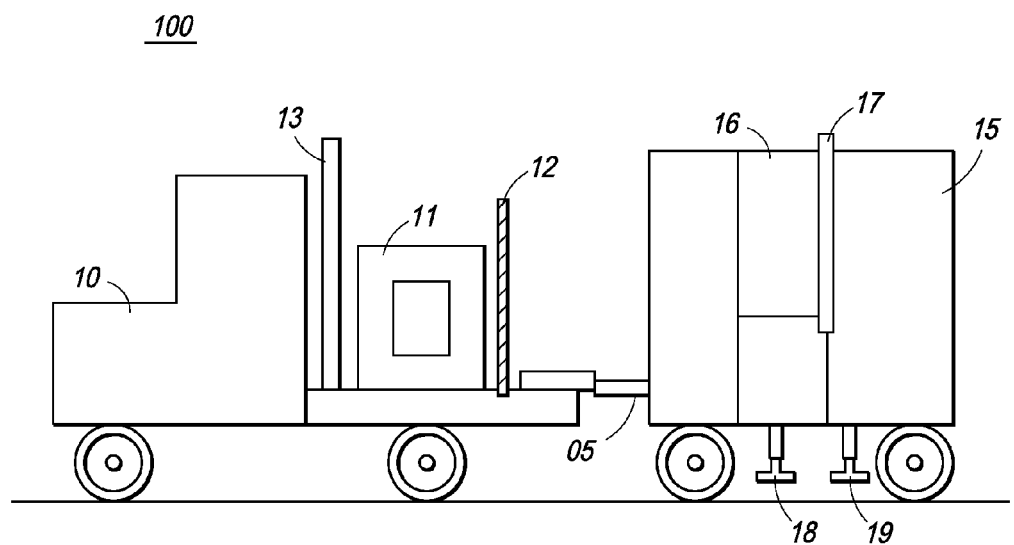
FIG. 1 provides a perspective view of an exemplary self-contained inspection system of the present invention.

In a first embodiment, FIG. 1 shows a perspective view of an exemplary self-contained inspection system 100. The system 100 comprises of an inspection module 15 that, in a preferred embodiment, is in the form of a mobile trailer capable of being towed and transported to its intended operating site with the help of a tug-vehicle 10. While the present invention is depicted as a tug vehicle 10 connected to a trailer 15, one of ordinary skill in the art would appreciate that the vehicular portion of the system and inspection module portion of the system could be integrated into a single mobile structure. The preferred embodiment uses a tug vehicle independent from the inspection module because, as discussed later, it adds greater flexibility in how the system is used. In another embodiment, the operator trailer, unit 15, could be a separate vehicle by itself.

The tug-vehicle 10 can serve as a support and carrier structure for at least one source of electromagnetic radiation 11; hydraulic lift system 12, such as the Hiab lifting cranes along with suitable jigs and fixtures or any other lifting mechanism known in the art, to load and unload the at least one source 11; and a possible radiation shield plate 13 on the back of the driver cabin of tug-vehicle 10, to protect the driver from first order scatter radiation. The inspection trailer 15 is hitched to the tug-vehicle 10 using a suitable tow or hitch mechanism 5 such as class I through V frame-mounted hitches; fifth wheel and gooseneck hitches mounted on the bed of a pick-up; a simple pintle-hitch; branded hitches such as Reese, Pull-rite and Hensley or any other means known to one of ordinary skill in the art. The class of the hitch indicates the amount of trailer load that it can handle. For example, a class I hitch is rated for a trailer load of about 2000 pounds whereas a class V hitch is rated for loads greater than 10,000 pounds. A typical manually-releasable tow-bar mechanism, disclosed in U.S. Pat. No. 5,727,806 titled "Utility Tow Bar" and assigned to Reese Products Inc., comprises a coupler assembly including a hitch ball receiving socket and cooperating lock. This facilitates selective connection of a tow-bar to the hitch ball of a trailer hitch receiver carried by a towing vehicle. Alternatively, automatic hitches may also be used for quick coupling and detaching of the tow truck and trailer without manual intervention or attendance.

Referring back to FIG. 1, the inspection or scanning module 15 is custom-built as a mobile trailer can provide support for a plurality of detector arrays 16 and a boom 17 to deploy a power cable to at least one source of radiation during operation. The trailer 15 also houses an operator/analyst cabin including computer and imaging equipment along with associated power supplies, air conditioning and power generating equipment in accordance with the understanding of a person of ordinary skill in the art of X-ray generation. In high energy/high performance system, the trailer containing the detector array 16 and boom 17 may be in a different unit from the trailer housing the operator inspection room 15. This will allow the operator to avoid being in a high radiation area and reduce the amount of shielding required for his protection. In preferred embodiment, the trailer 15 may additionally include a plurality of leveling or support feet 18, 19 to enable stabilized imaging when in stationary use.

In order to use the system 100, the inspection trailer 15 is towed to the inspection site by the tug-vehicle 10. After positioning the inspection trailer 15, the tug-vehicle 10 is detached and moved substantially parallel to the trailer 15 and towards the side carrying the detector system 16. Here, the radiation source box 11 is shifted out of the tug-vehicle 10 and lowered down to the ground by a hydraulic crane 12 mounted on the tug-vehicle 10. Thus, the source box 11 is placed laterally opposite to the detector system 16 at a distance that is suitable to allow an OUI to pass between the source 11 and detector 16 during the scanning process. An OUI could be any type of object, including cars, trucks, vans, mobile pallets with cargo, or any other type of moveable object. During the scanning process, the tug-vehicle 10, after lowering down the source 11, is maneuvered to attach to the OUI and tow the OUI through the radiation scan beam. As the OUI is towed through the radiation beam, an image of the OUI is produced on the inspection computers housed within the trailer 15 showing the radiation-induced images of the articles and objects contained within the OUI.

Figure 2:
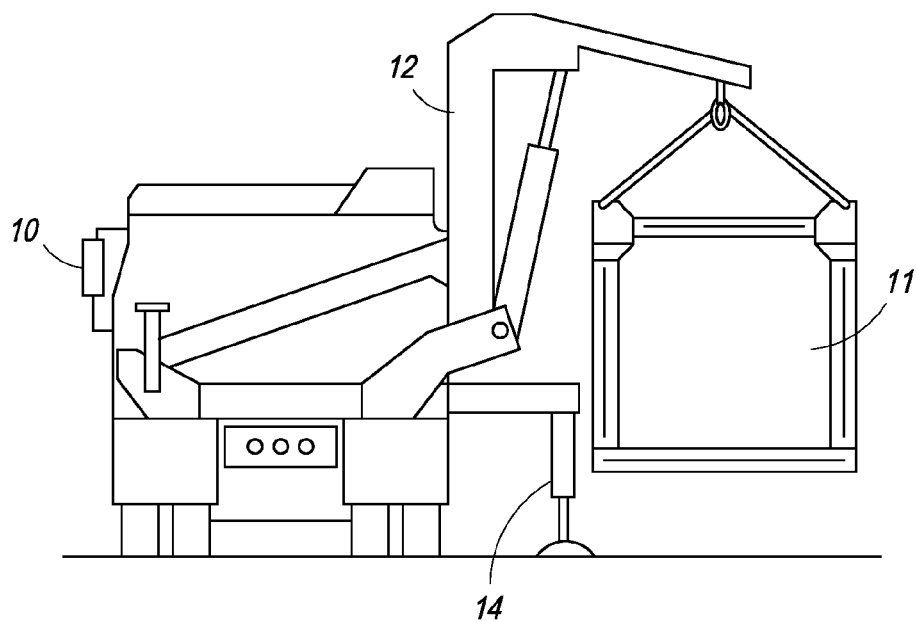
FIG. 2 depicts one embodiment of a hydraulic lift mounted on a tug-vehicle and the unloading of a radiation source.

Referring to FIG. 2, a rear elevation view of a preferred embodiment of the tug-vehicle 10, depicting the unloading of source of radiation 11 using a lifting mechanism 12 is shown. As previously mentioned, in a preferred use of the system, the tug vehicle is separated from the trailer and driven to an area where the source is to be positioned, preferably largely parallel to the trailer and separated from the trailer by sufficient space to allow an OUI, such as a vehicle or container, to pass.

To allow for the safe and rapid deployment of the radiation source 11, a preferred embodiment uses stabilizing feet 14 to increase the base of the tug vehicle 10 and off load the stress from the wheels, as the source 11 is lifted off the tug-vehicle 10 using a suitable hydraulic lift 12 and brought down from the side for deployment. The radiation source 11 may be put into position using any means known to one of ordinary skill in the art, such as a wheeled platform. The hydraulic lift 12 puts the source box 11 on a wheeled platform so that the source can now be tugged and can be angularly rotated into a suitable position.

The source of radiation 11 includes radio-isotopic source, an X-ray tube or any other source known in the art capable of producing beam flux and energy sufficiently high to direct a beam to traverse the space through an OUI to detectors at the other side. The choice of source type and its intensity and energy depends upon the sensitivity of the detectors, the radiographic density of the cargo in the space between the source and detectors, radiation safety considerations, and operational requirements, such as the inspection speed. One of ordinary skill in the art would appreciate how to select a radiation source type, depending upon his or her inspection requirements. In one embodiment, where the OUI is a large sized container or car that highly attenuates the X-ray beam, the radiation could be from an X-ray tube operating at a voltage in substantial excess of 200 keV, and may operate in a region of approximately 4.5 MeV.

A further possibility for examining an OUI can be achieved by driving the radiation source 11 with respectively different radiation energies or by using two detector systems, having varying sensitivities to differing radiation energies. By comparing at least two congruent radiation images that were obtained with respectively different radiation energies, it could be possible to discriminate articles having low and high ordering number. Organic materials, such as drugs and explosives, can thus be better distinguished from other materials, for example metals (weapons).

Referring back to FIG. 2, while the tug vehicle has been moved, with the radiation source, to a position for the deployment of the radiation source, the inspection trailer is also being deployed. Now referring to FIG. 3, a side elevation view of the portable inspection trailer 15 is shown incorporating a boom 17 and a plurality of detectors 16 folded to the side of the trailer 15. The detectors 16 are preferably in a formation that, when folded or stored permit the trailer 15 to safely travel on public roadways. Additionally, the detectors 16 are preferably integrally formed to enable for stable, yet rapid deployment. The detectors may also be linear arrays that extend substantially parallel to the base of the trailer and, when deployed, extend substantially orthogonal to the base of the trailer.

Figure 3:
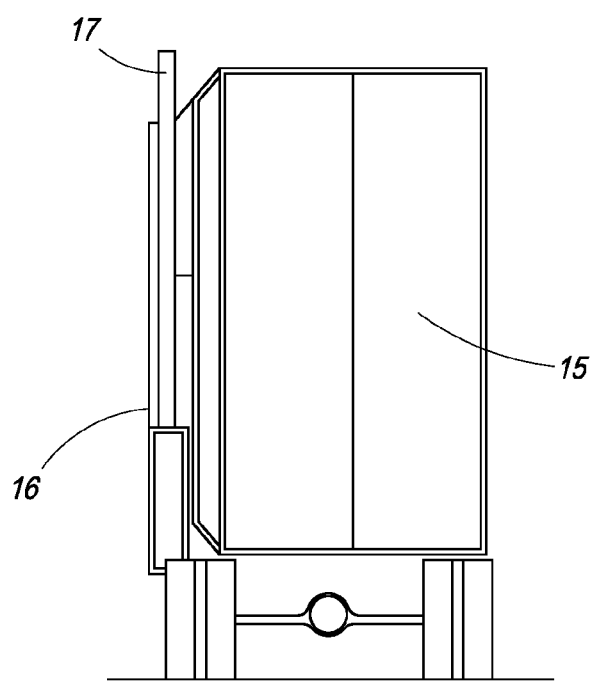
FIG. 3 is a side elevation view of one embodiment of the portable inspection trailer.
Figure 4:
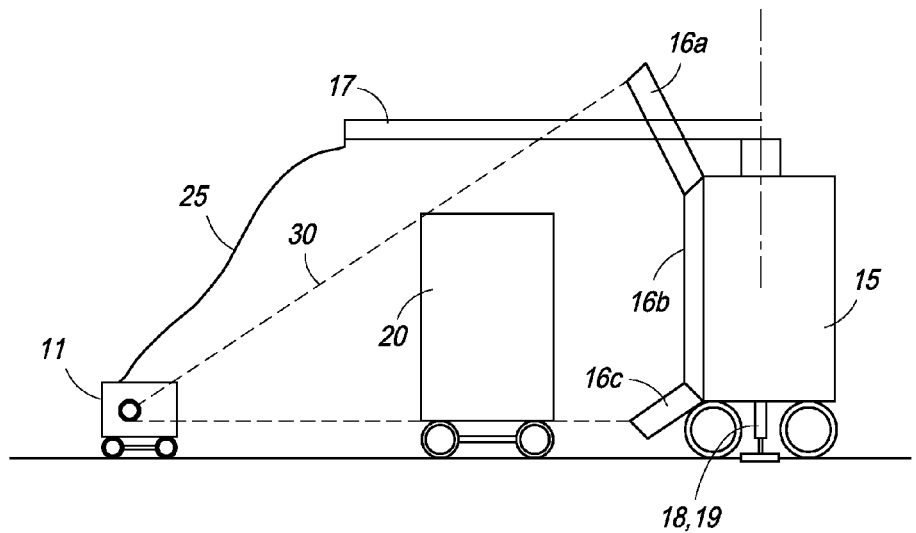
FIG. 4 is a side elevation view of one embodiment of the present invention in operational mode.

In one embodiment, as shown in FIG. 4, the detectors comprise three sections 16a, 16b and 16c that are capable of being folded, as earlier seen in FIG. 3, such that, when in a storage position, the detectors recess into the side of the inspection trailer 15. By forming detectors such that they can fold in a storage position, it is possible to produce a compact trailer 15 that can safely, and legally, travel roadways. When unfolded during operation, the detectors 16a, b and c, may assume a linear or an arched shape. In one embodiment the detectors assume an approximate "C" shape, as seen in FIG. 4. The preferred "C" shape allows for a shorter total height of detectors in folded position, minimizes alignment problem because top and bottom sections 16a, 16c are almost in the same line, provides a relatively smaller dose to all detectors and are less prone to damage by the effective overall height of the trailer 15. As shown, the detector sections 16a, 16b, and 16c are in alignment with a radiation source 11 that is powered through a power cable 25 attached to a boom 17. Within the area defined between the detector sections 16a, b, and c and the radiation source 11 is an OUI 20.

In order to facilitate push-button deployment and the dispensing away of assembling tools or skill, the action of folding or unfolding of the detectors 16a, 16b and 16c is managed by a suitable hydraulic system known to a person of ordinary skill in the art.

Figure 6:
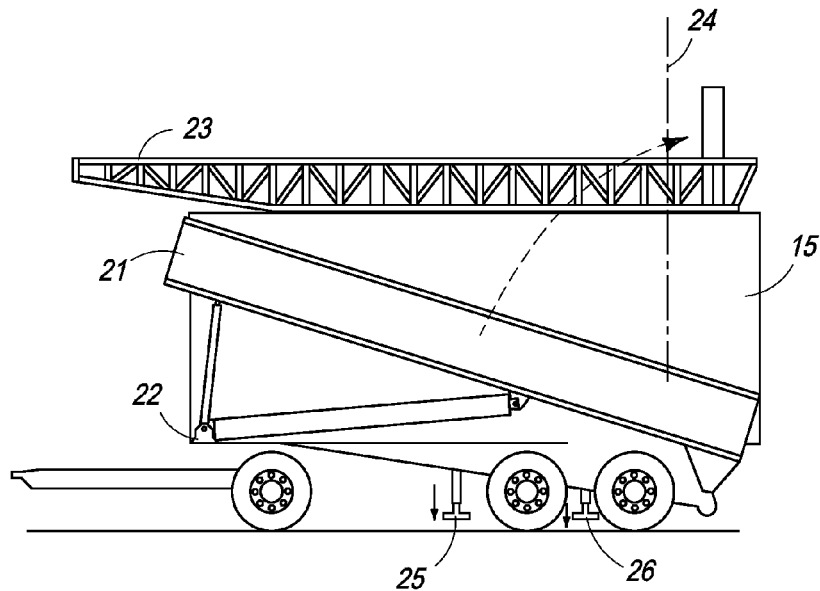
FIG. 6 is a second embodiment of an inspection trailer.
Figure 7:
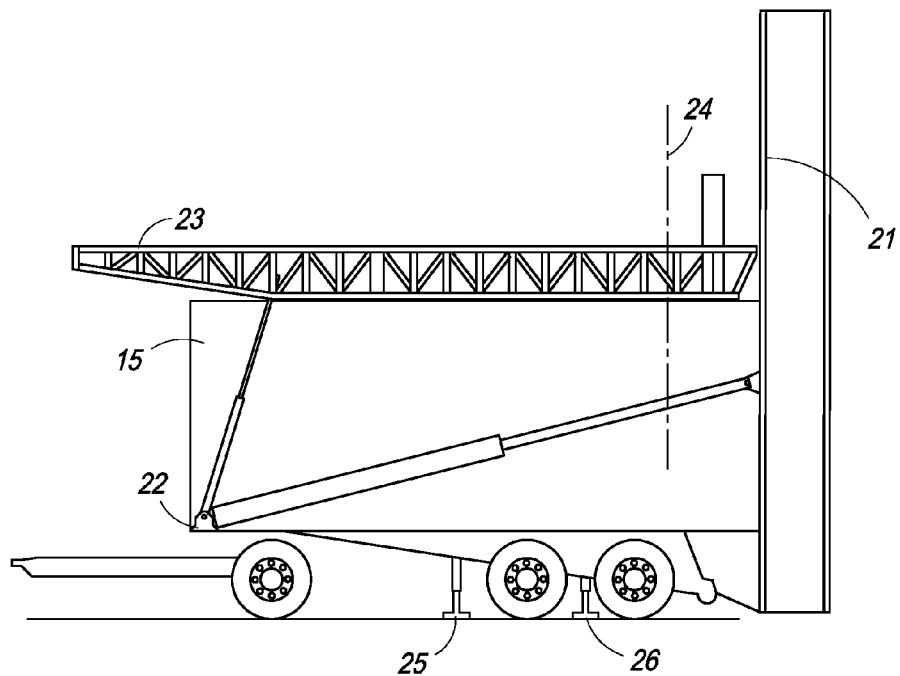
FIG. 7 is one embodiment of an inspection trailer, depicting the use of a hydraulic system.

FIGS. 6 and 7 show one embodiment of the inspection trailer 15, depicting the use of a typical hydraulic system 22 for deploying an exemplary array of linear-shaped detectors 21. During operation, the hydraulic mechanism 22, pushes the detectors 21 in a substantially vertical position while the stabilizing feet 25 and 26 are deployed downwards so that the trailer 15 now partially rests on them instead of just on the wheels, thereby minimizing movement and providing stability to the trailer 15 during the scanning operation. A boom 23, is also shown in a rest position lying on the top of the trailer 20, and pivoted at one end around a vertical axis 24, such that the boom 23 can rise and rotate orthogonally relative to the trailer 15 during deployment.

Figure 9A:
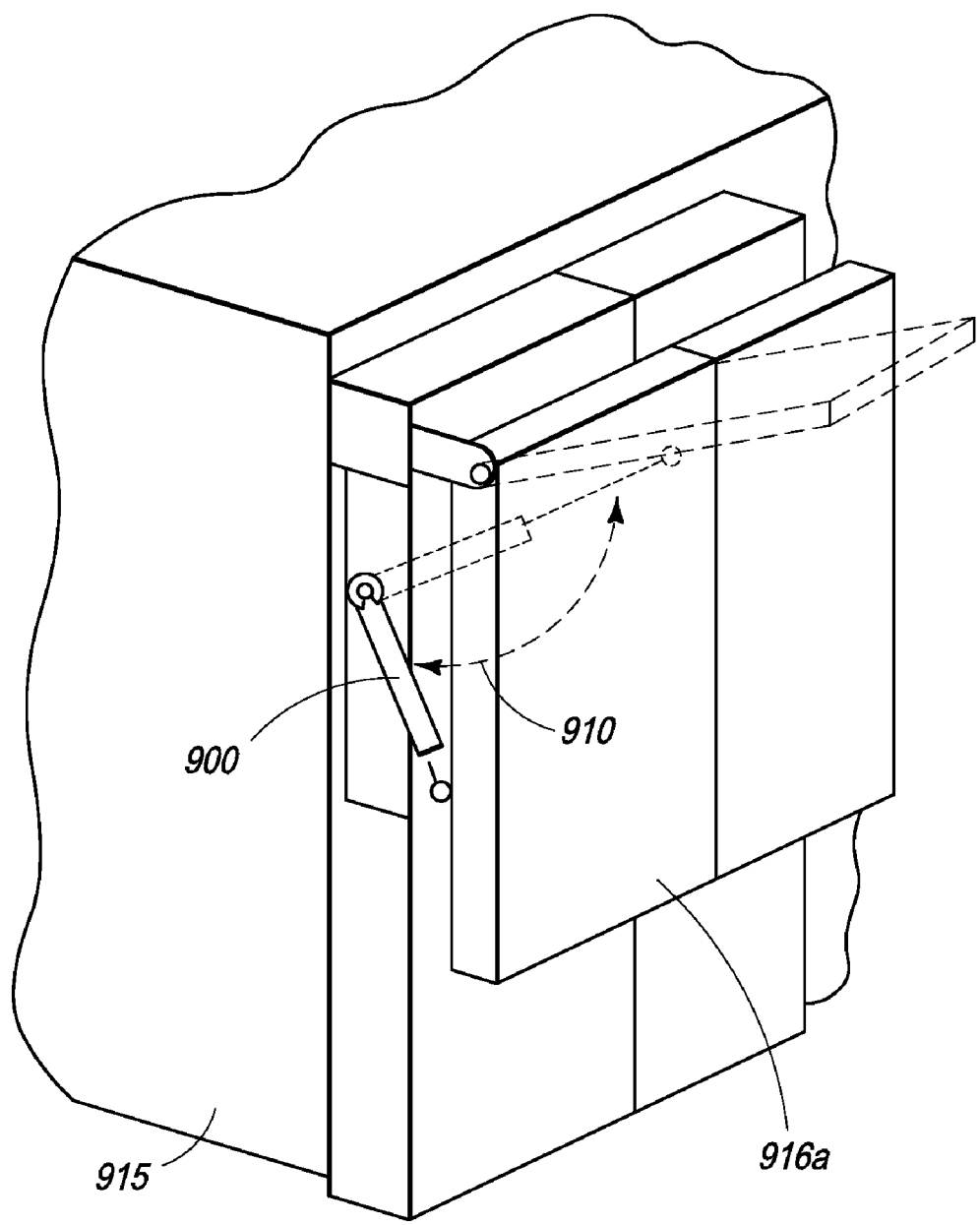
FIG. 9a is a schematic view of an exemplary hydraulic system used for automatically unfolding the detector panels.
Figure 9B:
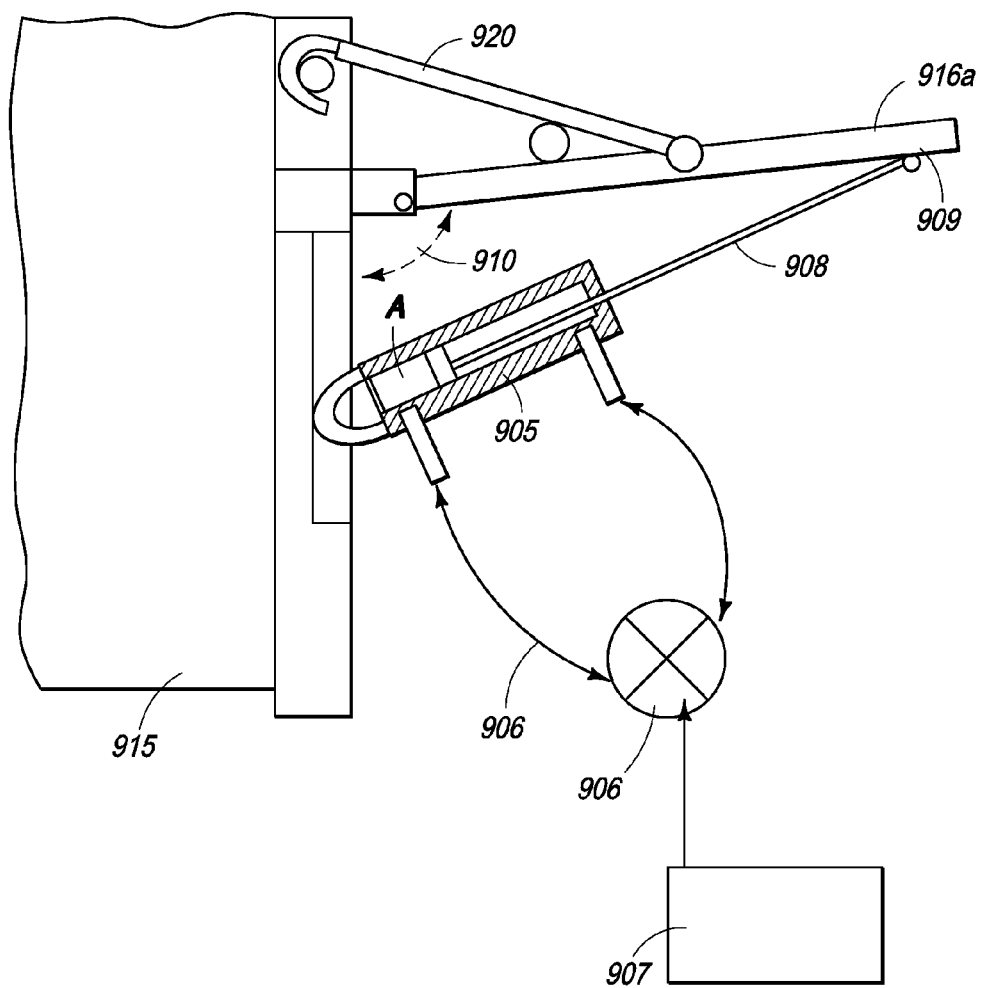
FIG. 9b is a second view of an exemplary hydraulic system used for automatically unfolding the detector panels.

In one embodiment, as shown in FIG. 4, the detectors 16 remain folded to a side of the trailer 15 in an approximately vertical position so that the associated hydraulic mechanism is only used to unfold the folded sections of the detector system 16. FIGS. 9a and 9b show an exemplary hydraulic system 900 used to unfold the top detector panel 916a. The hydraulic system 900 comprises a reversible electrical motor 907 to drive a hydraulic pump 906 that in turn provides hydraulic fluid under pressure to a double acting hydraulic actuator 905 attached to trailer 915. When the hydraulic actuator 905 is required to unfold the detector 916a, pressurized hydraulic fluid is pumped into chamber A, engaging piston 908 to move slider ball 909 that in turn unfolds the detector 916a. Once the detector 916a is unfolded through an acceptable angle 910 the detector 916a is securely latched in position using a mechanical latch 920 such as a simple hook and peg system or any other latching arrangement known to one of ordinary skill in the art. A similar arrangement can be used to deploy the lower detector panel.

The detectors 16 may be formed by a stack of crystals that generate analog signals when X-rays impinge upon them, with the signal strength proportional to the amount of beam attenuation in the OUI. In one embodiment, the X-ray beam detector arrangement consists of a linear array of solid-state detectors of the crystal-diode type. A typical arrangement uses cadmium tungstate scintillating crystals to absorb the X-rays transmitted through the OUI and to convert the absorbed X-rays into photons of visible light. Crystals such as bismuth germinate, sodium iodide or other suitable crystals may be alternatively used as known to a person of ordinary skill in the art. The crystals can be directly coupled to a suitable detector, such as a photodiode or photo-multiplier. The detector photodiodes could be linearly arranged, which through unity-gain devices, provide advantages over photo-multipliers in terms of operating range, linearity and detector-to-detector matching. In another embodiment, an area detector is used as an alternative to linear array detectors. Such an area detector could be a scintillating strip, such as cesium iodide or other materials known in the art, viewed by a suitable camera or optically coupled to a charge-coupled device (CCD).

Figure 8:
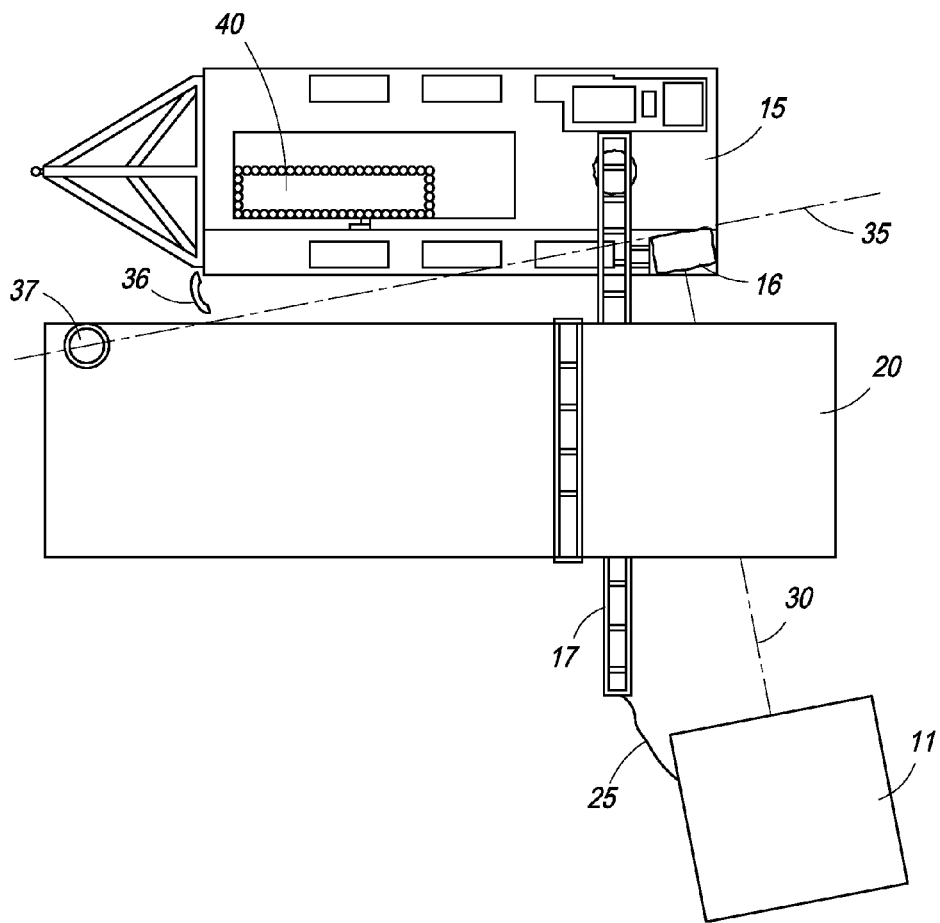
FIG. 8 is top plan view of a second embodiment of the present invention during operation.

FIG. 8 shows a plan view of the inspection trailer 15, associated image processing and control system 40 and an arrangement of detector system 16 as seen from the top. As shown, the plane of the detector system 16 represented by axis 35, is kept slightly skewed from the respective side of the trailer 15 by an angle 36, such as 10°, so that the angle between the trailer 15 and the path of the radiation beam 30 is substantially in excess of 90°. At angles of about 90° and above, relative to scatter location and beam path 30, the magnitude of first order scatter radiation is quite low. In the present system, when radiation is first emitted, the most likely scatter source is the detector system 16. Therefore the resulting relative angular position, between the axis 35 and beam path 30 due to the skew angle of the detector plane 35 from the trailer 15, helps in protecting driver 37 of the tug-vehicle 20 from radiations scattered by the detector system 16.

The X-ray image processing and control system 40, in an exemplary embodiment, comprises a computer and storage systems which records the detector snapshots and software to merge them together to form an X-ray image of the vehicle 20 which may further be plotted on a screen or on other media. The X-ray image is viewed or automatically analyzed by OUI acquisition system such as a CRT or monitor that displays the X-ray image of the vehicle 20 to an operator/analyst. Alternatively, the OUI acquisition systems may be a database of X-ray images of desired targets, such as automobiles, bricks or other shapes that can be compared with features in the image. As a result of this imaging, only articles that were not contained in the reference image of the container or vehicle 20 are selectively displayed to an operator/analyst. This makes it easier to locate articles that do not correspond to a reference condition of the container or vehicle 21, and then to conduct a physical inspection of those articles. Also, for high-resolution applications, the electronics used to read out the detector signals may typically feature auto-zeroed, double-correlated sampling to achieve ultra-stable zero drift and low-offset-noise data acquisition. Automatic gain ranging may be used to accommodate the wide attenuation ranges that can be encountered with large containers and vehicles.

Figure 10:
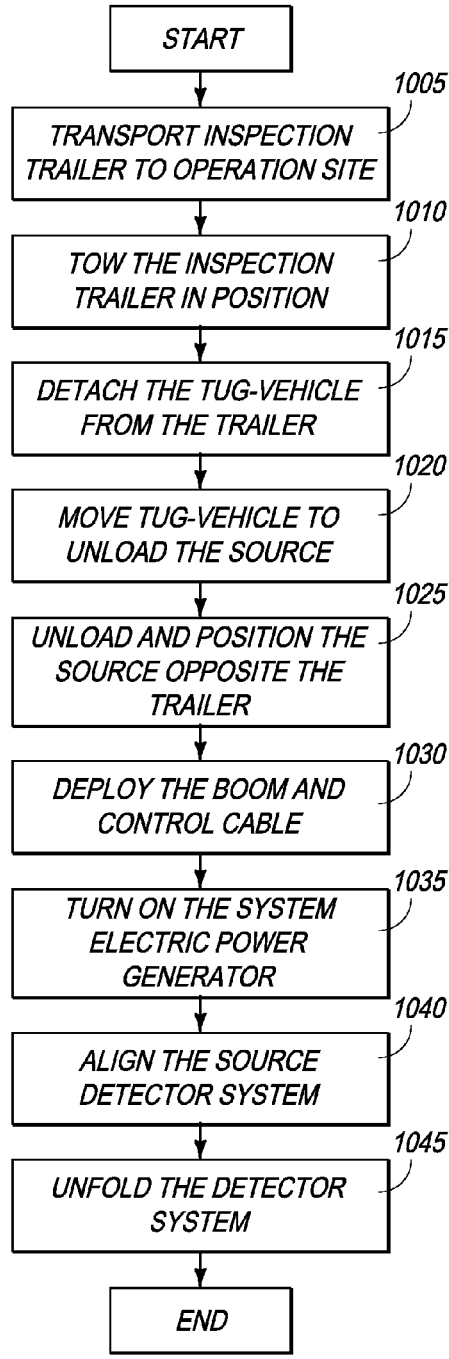
FIG. 10 is a flowchart of one exemplary process for setting-up the system of the present invention.

Referring now to FIG. 10, during deployment the inspection trailer is transported 1005 to the operation site and towed 1010 in position by the tug-vehicle. The trailer is advantageously positioned proximate to a cargo loading area so that the laden cargo containers can pass through the source-trailer system without disrupting port activities. One such preferable place for positioning the trailer could be an exit point of a port. Another aspect that may influence the decision of positioning the trailer could be the availability of a large enough area, called the "exclusion zone", around the scanner system. The exclusion zone is an area around the scanner in which general public are not authorized to enter due to the possibility of their getting exposed to doses of radiations scattered during the scanning process. The exclusion area is dependent upon the magnitude of current setting the intensity of the radiation source.

After positioning the trailer suitably, the tug-vehicle is preferably detached 1015 from the trailer. Next the tug vehicle is moved 1020 to an area proximate to and preferably parallel from the inspection trailer in order to unload and position the source of radiation. The source of radiation is then pulled 1025, or lowered, out of the tug-vehicle, using a hydraulic lift, and lowered down to the ground to be deployed laterally opposite to the side of the trailer supporting the detectors. The boom is also rotated 1030 substantially orthogonally from its rest position in order to deploy 1030 control cable to provide power and control signals to the source. The electrical power generator, housed in the trailer, is now turned on 1035 to provide power to the electrical devices in the system.

Figure 11:
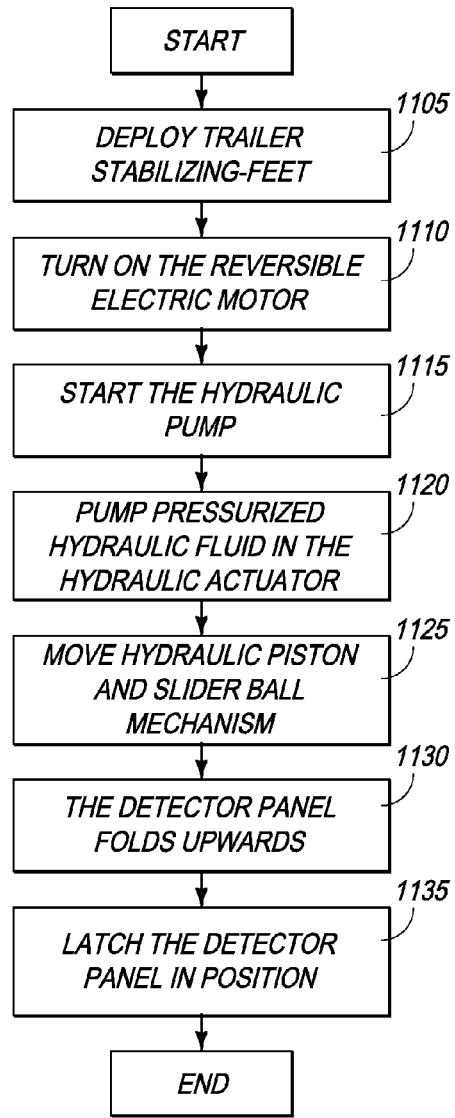
FIG. 11 is a flowchart of one exemplary process for deploying the detector system.

While the generator is deployed described above, the detectors are unfolded 1045. The detectors may be positioned in a variety of ways, as earlier described, including a linear or, using a suitable hydraulic mechanism, in an approximate "C" shape. Shown in FIG. 11 is a process flow diagram of the detector deployment process. Stabilizing feet are first deployed 1105 to provide stability to the trailer as it deploys the detector structure. One of ordinary skill in the art would appreciate that the objective of deploying stabilizing feet is to widen the trailer support base and distribute weight to increase stability and lessen the likelihood of tipping. Other mechanisms could be used to stabilize the trailer structure, including, for example, a hydraulic jack that lifts the trailer up so that the trailer now rests on a support platform instead of on the wheels; hydraulic brakes that are engaged once the trailer has been suitably positioned such that the brakes cusp the trailer wheels preventing any movement of the wheels; or simply a pair of wheel-stops that can be manually placed in front and at the rear of front and rear wheels respectively preventing any translational motion of the wheels.

Once the trailer is stable, the reversible electric motor of the detector hydraulic system is turned on 1110. The motor starts 1115 the hydraulic pump that fills 1120 the hydraulic actuator with pressurized hydraulic fluid. This moves 1125 the hydraulic piston, attached to the detector through a slider ball, causing the detector to unfold 1130 upwards. After unfolding the detector panel to a suitable position, the detector panel is latched 1135 in order to hold it in the required unfolded position. A similar process is carried out to unfold the bottom panel of the detector system.

Once the radiation source box is placed opposite to the detector array and the array box is fully deployed, alignment 1040 steps are carried out comprising of: adjusting the vertical height of the radiation source box using leveling mechanisms such as leveling screws or any other leveling means known to a person of ordinary skill in the art; and alignment of the radiation beam with respect to the detectors.

Figure 12:
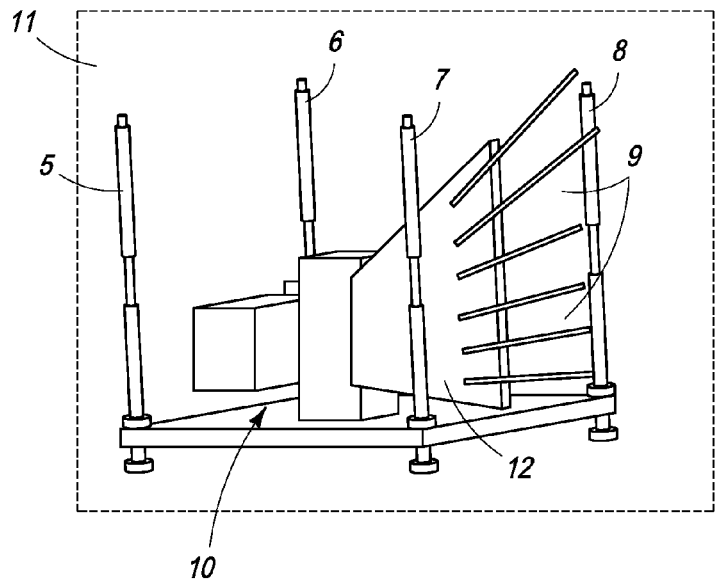
FIG. 12 is a view of an exemplary radiation source box.

FIG. 12 is an exemplary embodiment of the radiation source box 11, showing leveling screws 5, 6, 7 and 8 that can be turned to manipulate the vertical height of the source box 11 and an array of laser pointers 9 built into the collimator 10 to facilitate proper alignment of the radiation beam 12 with the detectors. In one embodiment, optical triangulation method is used for aligning the plane of the radiation beam with a predefined "zero" or "idealized centerline" of the detector system. Such optical triangulation techniques, as known to a person of ordinary skill in the art, use a source of light such as a laser pointer to define the radiation beam path. These laser pointers are directed to impinge on a predefined "zero" of the detectors. The "zero" of the detectors maybe a spot representing the centroid of the detector system or an idealized centerline representing a spatial x-y locus of an ideal fan beam plane intersecting the plane of the detectors substantially orthogonally. In one arrangement, the spatial position of the laser pointers impinging on the detectors is sensed by an array of photo-electric diodes of the detector system that send the corresponding position signals to a computer housed within the trailer. The computer compares the spatial position of the laser pointers with a predefined "zero" of the detector system and sends correction control signals to the source box through the control cable (attached to the boom) for adjustments till the laser pointers are reasonably lined-up with the detector system Depending on conditions, other system elements may be deployed to enable the screening process. Such elements may include surveillance systems such as the closed-circuit television (CCTV) to monitor area around the scanner to control the exclusion zone, a lighting system and a wireless network. The lighting system may be required to facilitate night operation. In a preferred embodiment the analysis of the scanned images of an OUI are done by an analyst seated inside the inspection trailer. However, in another embodiment a separate command center may alternatively or additionally be located away from the scanner, preferably outside the exclusion zone, where a similar analysis of scanned images may be done. In such an arrangement wireless networks may additionally be needed to transfer data from the scanner system to the command center.

After deploying the system as described above, an operator may undertake the following procedure to examine an OUI using the present invention. As used in this description, an OUI is any receptacle for the storage or transportation of goods, and includes freight pallets as well as vehicles, whether motorized or drawn, such as automobiles, cabs and truck-trailers, railroad cars or ship-borne containers and further includes the structures and components of the receptacle.

Figure 5:
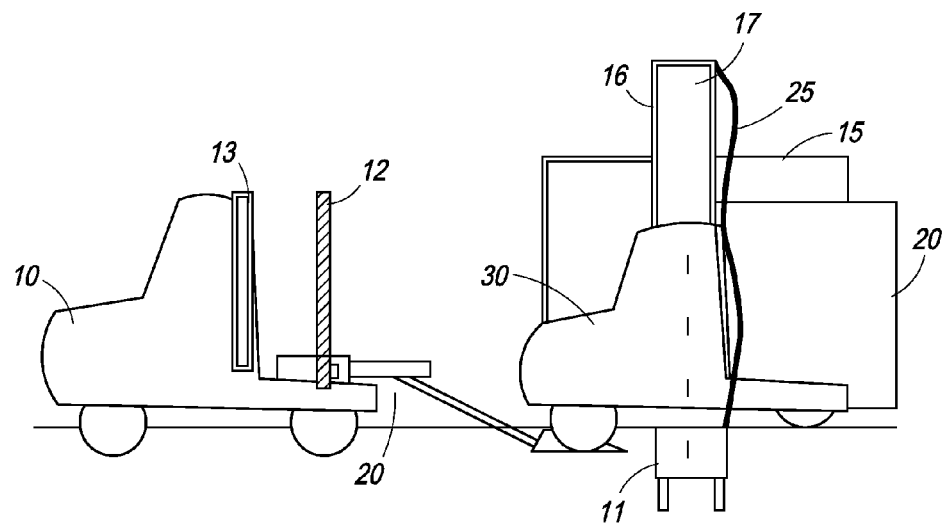
FIG. 5 is a side view of a second embodiment of the present system.

Referring back to FIG. 5, a side elevation view of the system of one embodiment of the invention during operation is shown. The OUI in this illustration is a vehicle 20 that is being towed between the source 11 and detectors 16 by the tug-vehicle 10. In a preferred arrangement the tug-vehicle 10 is the same vehicle that was earlier used to transport the inspection trailer 15 to the site. Thus the tug-vehicle 10 serves the twin purpose of not only transporting the inspection trailer 15 but also to tow an OUI, such as vehicle 20, during the scanning process to provide a relative motion between an OUI and the source 11/detector 16 system. The mechanism used to attach the tug-vehicle 10 to the trailer 15 and then to an OUI during operation may be different. For example, one or more wheel catchers 22 that cups one or more wheels of an OUI, thereby allowing the tug vehicle 10 to pull the OUI by dragging the wheel catcher 22, may be used to tow the inspected vehicle 20. Similarly, other attachment mechanisms may alternatively be used, as would be known to persons ordinarily skilled in the art.

During the scanning operation, the source 11 and detectors 16 remain stationary and aligned with respect to each other while the OUI, which is a vehicle 20 in this case, is made to move. In a preferred embodiment, the motion of the vehicle 20 is kept steady and at a constant velocity such as at or around 2 km/hr. Since, irregularities in the motion of the vehicle 20 may result in distortions in the scanned image, the motion is preferably made as regular, even and constant as feasible using known control systems such as by engaging the tug-vehicle 10 in "auto speed" mode. In alternate embodiments, to scan at varying speeds depending on the speed of the tug-vehicle 10, irregularities of motion are measured and the radiographic image is correspondingly corrected. To accomplish this, a telemetry mechanism may be used to relay the speed of the tug-vehicle 10 to the inspection trailer 15. For example, one or more motion encoders can be affixed to one wheel of the tug-vehicle 10. An encoder measures the rotational velocity of the wheel and transmits a corresponding electrical signal to the imaging system's computer housed within the inspection trailer 15. If there is a change in speed, the computer automatically includes a corresponding compensation in the timing of the detector signals for that location, thereby eliminating image distortions induced due to non-uniform motion of the tug-vehicle 10.

Start-sensors, not shown, are strategically placed to allow an imaging and control system, located within the inspection trailer 15, to determine that the tug-vehicle 10 has passed the area of beam and the vehicle 20 to be inspected is about to enter the X-ray beam position 30. Thus, as soon as the vehicle 20 to be inspected trips the start-sensors, the radiation source 11 is activated to emit a substantially planar fan-shaped or conical beam 30 (for the duration of the pass) that is suitably collimated for sharpness and made to irradiate substantially perpendicular to the path of the vehicle 20.

Since the source 11 and detector 16 remain stationary during the scanning process, collimation can be adjusted to an advantageous minimum such that the fan beam emerging out of the collimator just covers the detectors 16. Apart from using a collimator at the source of radiation, in an alternate embodiment, another collimator arrangement can be additionally provided integral to the detector system 16 so that the width of the fan beam finally striking the detectors 16 may be further changed. As known in the art, X-ray scanning operates on the principle that, as X-rays pass through objects, some get stopped, some pass through, and some get deflected owing to a number of different physics phenomena that are indicative of the nature of the material being scanned. In particular, scattering occurs when the original X-ray hits an object and is then deflected from its original path through an angle. These scatter radiations are non-directional and proportional to the total energy delivered in beam path. A narrowly collimated beam will keep the overall radiation dose minimal and therefore also reduce the amount of scatter radiation in the area surrounding the scanner. This, in one arrangement, is achieved by using an adjustable collimator with a long snout.

Also, the fan angle of the fan beam 30 is wide enough so that the radiation from the source 11 completely covers the cross section of the vehicle 20 from the side and the radiation is incident on the approximately "C"-shaped radiation detectors 16. It would also be possible to make the fan angles of the source 11 smaller than would be necessary to encompass the entire cross-section of the articles being inspected, in which case the source 11 could be mounted so as to be pivotable around an axis that is essentially parallel to the direction of motion of the vehicle 20. Thus, by pivoting the source 11, the entirety of the cross section of the vehicle 20 can be penetrated by the radiation.

At any point in time when the source 11 is on, the detectors 16 are snapshots of the radiation beam attenuation in the vehicle 20 for a particular "slice" of the vehicle 20 under inspection. Each slice is a beam density measurement, where the density depends upon beam attenuation through the vehicle 20. The radiation detectors 16 convert the lateral radiation profile of the vehicle 20 into electrical signals that are processed in an image processing system, housed in the inspection trailer 15, while the vehicle 20 is being conducted past the source 11 and the radiation detector 16.

In a second embodiment, the present invention is directed towards a relocatable cargo inspection system that employs a single boom attached to a truck that is capable of receiving and deploying the boom. The boom comprises a plurality of radiation detectors and a source. The boom is preferably installed in the rear of the truck to minimize radiation dosage to the driver and is capable of being folded into the truck and folded out, thus forming an inverted "L" on either the driver or passenger side.

The single boom structure permits the source, positioned at the base of the connecting structure, to rigidly align with the detector array, also permitting the unit to operate with a narrower beam width and a lower radiation level. In addition, the position of the source at the base of the connecting structure enables a larger field of view relative to conventional systems having the source on the vehicle. The source preferably extends to a height as low as six inches off the ground. Reference will now be made in detail to specific embodiments of the invention. While the invention will be described in conjunction with specific embodiments, it is not intended to limit the invention to one embodiment.

Figure 13:
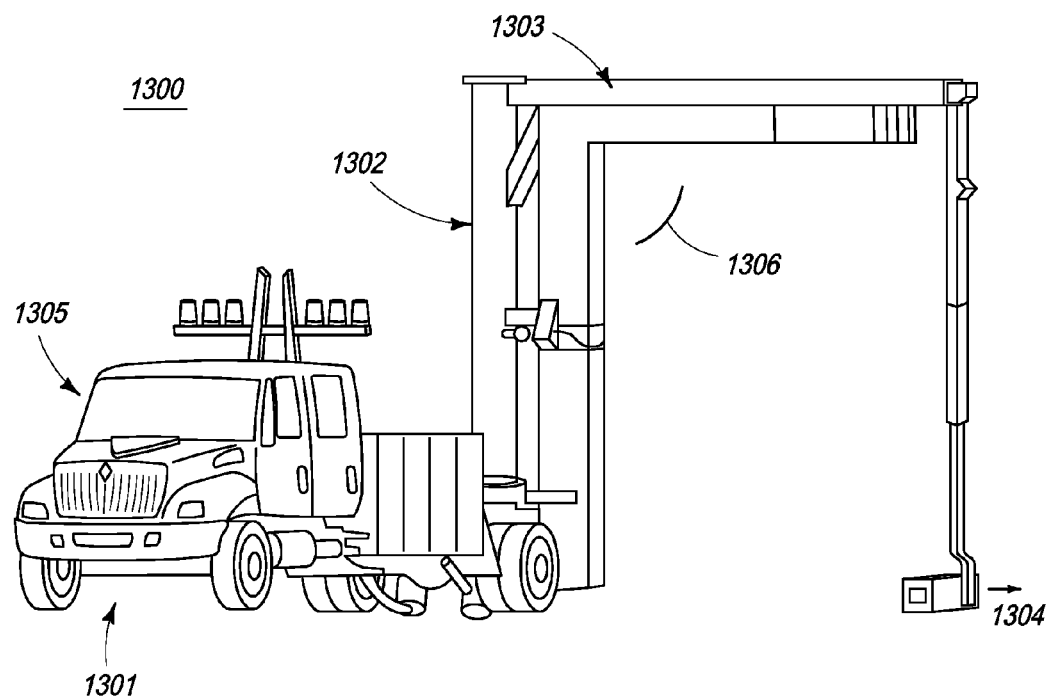
FIG. 13 is a representation of an exemplary embodiment of the integrated single boom cargo scanning system of the present invention.

Referring to FIG. 13, the schematic representation of an exemplary embodiment of the integrated single boom cargo scanning system of the present invention is depicted. The self-contained inspection system 1300 of the present invention comprises, in a preferred embodiment, an inspection module in the form of a rig/tractor trailer 1301, capable of being driven to its intended operating site. The vehicular portion of the system and the inspection module portion of the system are integrated into a single mobile structure. The integrated modular mobile structure serves as a support and carrier structure for at least one source of electromagnetic radiation; and a possible radiation shield plate on the back of the driver cabin of the vehicle, used to protect the driver from first order scatter radiation.

The inspection or scanning module 1300 is custom-built as an integrated mobile trailer 1301 and can provide support for a single boom 1302 to deploy a power cable (not shown) to at least one source of radiation 1304 during operation. In one embodiment, the at least one source of radiation is capable of emitting radiation of at least one energy. In one embodiment, the at least one source of radiation is capable of emitting radiation in two different energies. In another embodiment, the inspection or scanning module 1300 can provide support for two sources of radiation 1304. The operational characteristics of using two sources of radiation 1304 having two different energies are discussed in greater detail below with respect to FIGS. 27-29.

Now referring back to FIG. 13, boom 1302 additionally houses an array of detectors 1303. In a preferred embodiment, boom 1302 is attached to trailer 1301, capable of receiving and deploying the boom. Boom 1302 is preferably installed and located in the back of trailer 1301 to minimize radiation dosage to driver in trailer cab 1305. Trailer 1301 also houses an operator/analyst cabin including computer and imaging equipment along with associated power supplies, air conditioning and power generating equipment (not shown) in accordance with the understanding of a person of ordinary skill in the art of X-ray generation. Depending on conditions, other system elements may be deployed to enable the screening process. Such elements may include surveillance systems such as the closed-circuit television (CCTV) to monitor area around the scanner to control the exclusion zone, a lighting system and a wireless network. The lighting system may be required to facilitate night operation. In a preferred embodiment the analysis of the scanned images of an OUI are done by an analyst seated inside the inspection trailer. However, in another embodiment a separate command center may alternatively or additionally be located away from the scanner, preferably outside the exclusion zone, where a similar analysis of scanned images may be done. In such an arrangement wireless networks may additionally be needed to transfer data from the scanner system to the command center. In addition, boom 1302 is capable of being folded into trailer 1301 in a "stowed" position or folded out from trailer 1301 in a "deployed" position, on either the driver or passenger side.

The radiation source box 1304 is located on the same single boom 1302 as the detection system 1303. Thus, while source box 1304 is located opposite the detector system 1303 at a distance that is suitable to allow Object under Inspection ("OUI") to pass in the area 1306 between the source 1304 and detector array 1303 during the scanning process, it is located on the same boom 1302 to eliminate the need for alignment. In one embodiment, the radiation source is an X-ray generator. In yet another embodiment, the radiation source is a linear accelerator (LINAC). If the X-ray generator or LINAC is mounted on the same single boom as the detector arrays, the need for sophisticated alignment systems each time the system is deployed is eliminated. Thus, the radiation source and detectors are substantially permanently aligned on the same single boom. The feature also allows for scanning at various degrees of offset, again without the need to realign the LINAC or X-ray generator and detectors.

An OUI could be any type of object, including cars, trucks, vans, cargo containers, mobile pallets with cargo, or any other type of cargo object. During the scanning process, the OUI remains in the area demarcated by the deployed boom 1306 as a fixed piece of cargo while the self-contained inspection rig/tractor trailer 1300 moves over the OUI. Alternatively, the self-contained inspection rig/tractor trailer 1300 can remain in place while a piece of cargo is driven, moved, dragged, tagged, and/or lifted through the scanning region 1306. As the self-contained inspection trailer 1300 is moved over OUI, an image of the OUI is produced on the inspection computers housed within the trailer showing the radiation-induced images of the articles and objects contained within the OUI (not shown). Therefore, in a preferred embodiment, the system is designed such that the self-contained inspection trailer moves over the stationary object (OUI).

The source of radiation includes radio-isotopic source, an X-ray tube, LINAC or any other source known in the art capable of producing beam flux and energy sufficiently high to direct a beam to traverse the space through an OUI to detectors at the other side. The choice of source type and its intensity and energy depends upon the sensitivity of the detectors, the radiographic density of the cargo in the space between the source and detectors, radiation safety considerations, and operational requirements, such as the inspection speed. The system of the present invention could employ source-based systems, for example, cobalt-60 or cesium-137 and further employ the required photomultiplier tubes (PMT) as detectors. If a linear accelerator (LINAC) is optionally employed, then photodiodes and crystals are used in the detector. One of ordinary skill in the art would appreciate how to select a radiation source type, depending upon his or her inspection requirements.

In one embodiment, where OUI is a large sized container or car that highly attenuates the X-ray beam, the radiation could be from an X-ray tube operating at a voltage in substantial excess of 200 keV, and may operate in varying regions, including 450 keV, 3 MeV, 4.5 MeV, and even, but not limited to 6 MeV.

In one embodiment, the present invention employs dual source-based systems and further employs the required photomultiplier tubes as detectors. In one embodiment, $^{60}$Co is used as a first gamma ray source and has a high specific activity of the order of 11.1 TBq (300 Ci) and a linear dimension of the active area of 6 mm. In one embodiment, the second gamma ray source is a 1.0, 1.6 or 2.0 Curie shuttered mono-energetic source of $^{137}$Cs gamma rays, having a 662 keV energy.

In another embodiment, a nearly mono-energetic $^{60}$Co gamma ray source is used, which is capable of emitting photons at two distinct energy levels, more specifically, 1170 and 1339 KeV. In one embodiment, the gamma rays emitted from the 60Co source are collimated by their slits to form a thin fan-shaped beam with a horizontal field angle of 0.1° and a vertical field angle of 80°.

Figure 14:
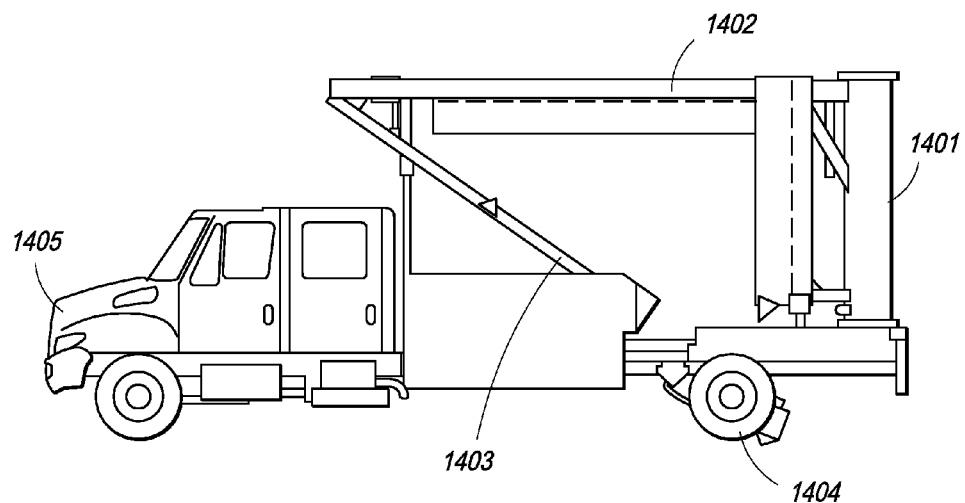
FIG. 14 is a side view illustration of one embodiment of the vehicle of the present invention in a "stowed" position.
Figure 15:
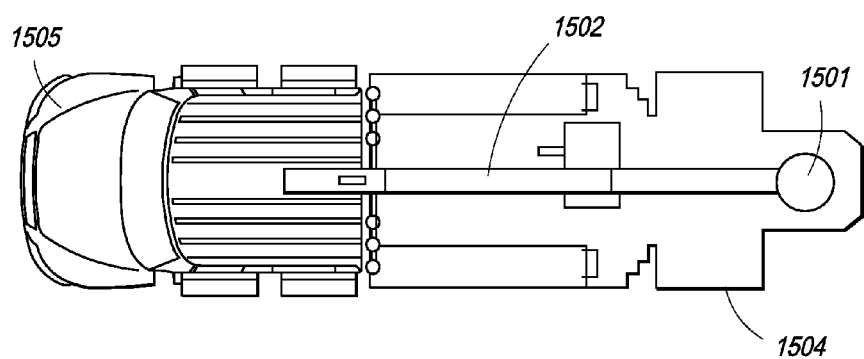
FIG. 15 is a top view illustration of one embodiment of the vehicle of the present invention in a "stowed" and relocatable position.

FIGS. 14 and 15 depict a side view illustration and top view illustration, respectively, of one embodiment of the vehicle of the present invention in a folded, or "stowed" position. In this position, the single boom 1401, 1501 detector arrays 1402, 1502 and radiation source 1403 fold onto the flatbed 1404, 1504 of the vehicle/trailer 1405, 1505. Thus, the detector arrays 1402, 1502 and radiation source 1403 are preferably positioned in a manner, such that when folded or stored, permit trailer 1405, 1505 to travel safely on public roadways. Additionally, the detectors are preferably integrally formed to enable for stable, yet rapid deployment. The detectors may also optionally be linear arrays that extend substantially parallel to the base of the trailer and, when deployed, extend substantially orthogonal to the base of the trailer.

Figure 16:
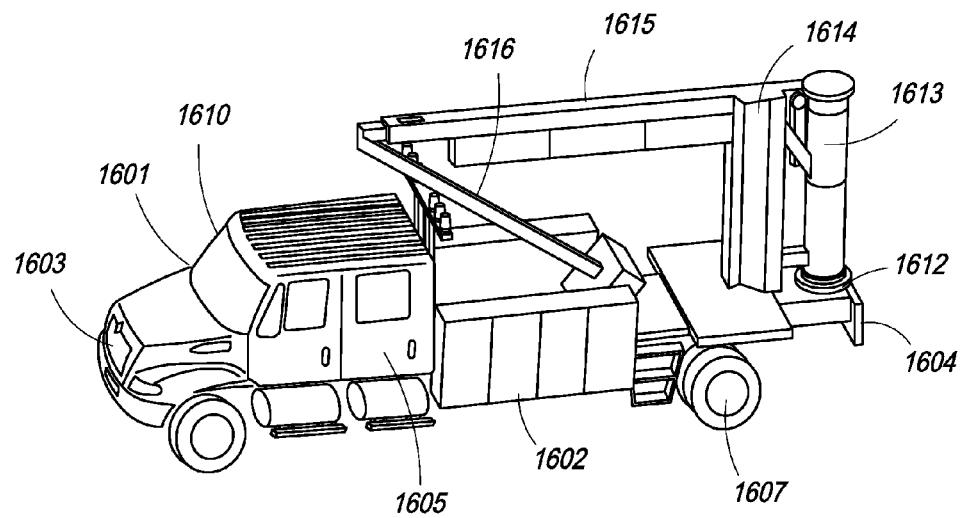
FIG. 16 is a side perspective view of the single boom cargo scanning truck of the present invention in a preferred embodiment.

Referring to FIG. 16, a side perspective view of the single boom cargo scanning system of the present invention in a stowed or "folded" position is depicted. In one embodiment, trailer 1601 comprises chassis 1602, having a front face 1603, a rear end 1604, and sides 1605. Trailer 1601 also comprises a trailer (driver's) cab 1610 and a single boom 1611. In a preferred position, boom 1611 extends centrally above chassis 1602 from a point (shown as 1612) approximately above rear axle 1607, thus allowing it to rotate in the desired directions. Boom 1611 has a proximal end attached to the vehicle and a distal end physically attached to the radiation source. Boom 1611 preferably consists of a hollow cylindrical main body 1613, a connecting structure 1614, an outer arm 1615, and a telescopic arm 1616. Outer arm 1615 protrudes from the connecting structure 1614 to preferably form an L-shaped structure. Both outer arm 1615 and connecting structure 1614 comprise detector panels (not shown).

Outer arm 1615 is further connected to telescopic arm 1616. Hydraulic cylinders or actuators (not shown) are provided for the turning movement of boom 1611, outer arm 1615 and telescopic arm 1616. In order to facilitate push-button deployment and the dispensing away of assembling tools or skill, the action of folding or unfolding of the outer arm 1615 containing the detector array is enabled by a suitable hydraulic system known to a person of ordinary skill in the art. One exemplary hydraulic system for unfolding the detector panels comprises a reversible electrical motor to drive a hydraulic pump that in turn provides hydraulic fluid under pressure to a double acting hydraulic actuator attached to the trailer. When the hydraulic actuator is required to unfold the detector panel, pressurized hydraulic fluid is pumped into the chamber, engaging a piston to move a slider ball that in turn unfolds the detector panel. Once the detector panel is unfolded through an acceptable angle, the detector panel is securely latched in position using a mechanical latch such as a simple hook and peg system or any other latching arrangement known to one of ordinary skill in the art. A similar arrangement can be used to deploy the remaining detector panels.

Figure 17:
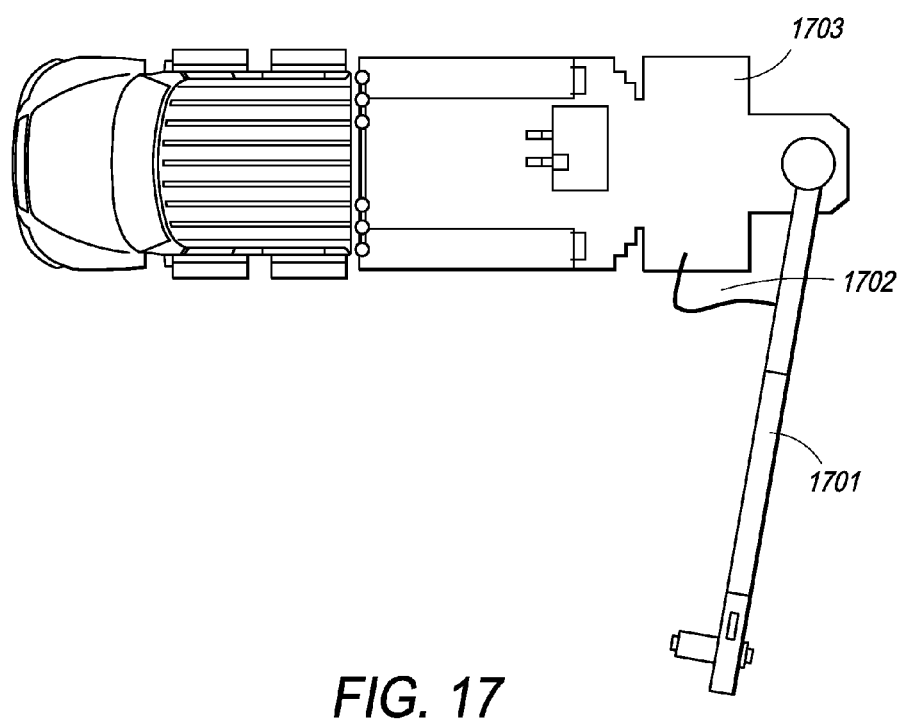
FIG. 17 depicts the top view of the single boom cargo scanning system of the present invention, in a deployed position.

FIG. 17 depicts a top view of the single boom cargo scanning system of the present invention, in a partially deployed or "partially unfolded" position. Outer arm 1701 is visible and open, thus forming angle 1702 with respect to trailer 1703. In one embodiment, the radiation source box (not shown) is located on the same single boom as the detector boxes (as described above) eliminating the need for sophisticated alignment systems each time the system is deployed. Thus, the radiation source is permanently fixed in alignment relative to the detector boom. The radiation source is located on one side of the boom while the detectors are located on the other. The rotating boom allows for the source of radiation to be positioned opposite the area of the boom supporting the detectors. The radiation source is rotated from a stored or stowed position to a deployed position. The electrical power generator is turned on to provide power to the electrical devices in the system. While the generator is deployed, the detectors are unfolded as described above.

Figure 18:
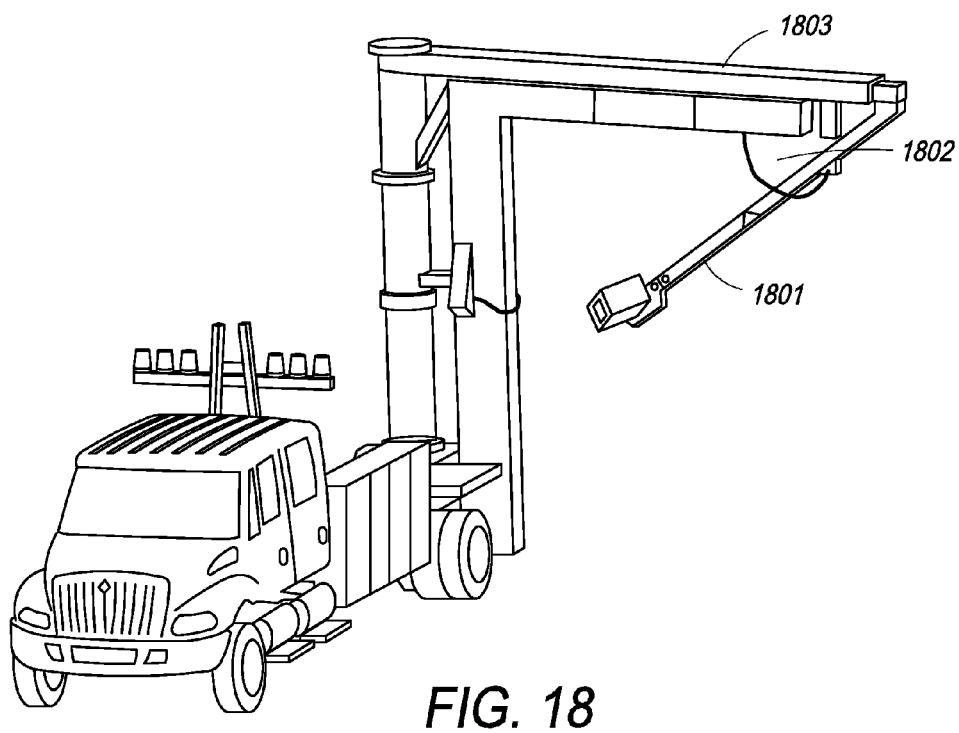
FIG. 18 depicts an exemplary movement of the telescopic arm of the single boom cargo scanning truck of the present invention.
Figure 19:
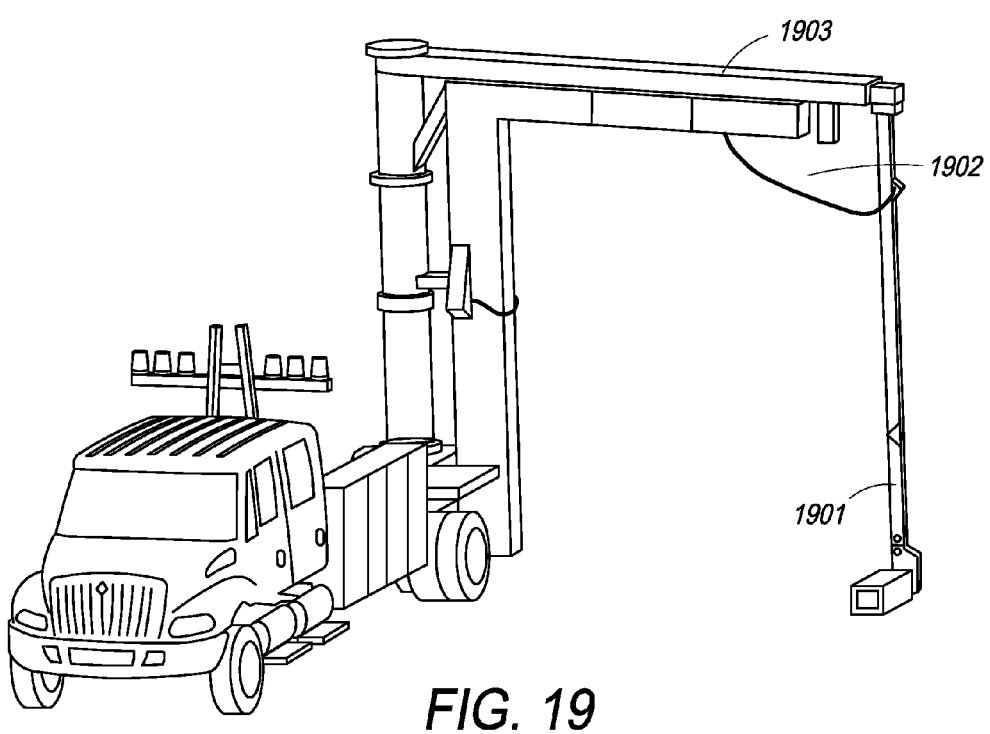
FIG. 19 depicts a second exemplary movement of the telescopic arm of the single boom cargo scanning truck of the present invention.

Referring back to FIG. 16, extension and withdrawal of telescopic arm 1616 in relation to the main body 1613 is preferably effectuated hydraulically using suitable hydraulic cylinders (not shown) in main body 1613. Thus, telescopic arm 1616 moves with multiple degrees of freedom. FIG. 18 depicts one exemplary movement of the telescopic arm 1801 of the single boom cargo scanning system of the present invention. Telescopic arm 1801 forms an acute angle 1802 with respect to outer arm 1803. In FIG. 19, another degree of freedom of the abovementioned telescopic arm is depicted. The telescopic arm 1901 is at a perpendicular 1902 to the outer arm 1903.

As described in detail above, the detectors optionally comprise panels that are capable of being folded, such that, when in a storage position, the detectors recess into the side of the inspection trailer. By forming detectors such that they can fold in a storage position, it is possible to produce a compact trailer that can safely, and legally, travel roadways. When unfolded during operation, the detectors assume either a linear or an arched shape.

Figure 20:
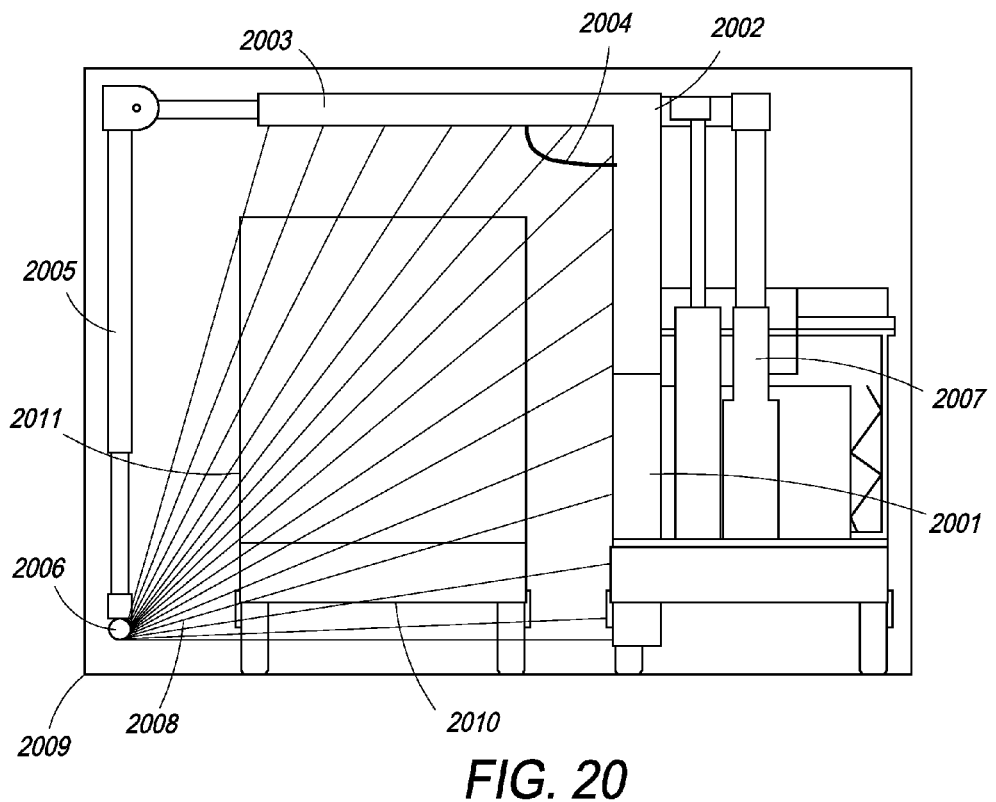
FIG. 20 is a rear view illustration of the single boom cargo scanning system of the present invention, in a preferred usage.

Now referring to FIG. 20, a rear view illustration of the single boom cargo scanning system of the present invention is depicted. As mentioned above, connecting structure 2001 and outer arm 2002 consist of detector array panels 2003. In one embodiment, the detectors assume an approximate inverted "L" shape, as they are placed on connecting structure 2001 and outer arm 2002. The inverted "L" shape detector enables the radiation source to be closer to the target vehicle, thus allowing higher penetration capability, and provides for complete scanning of the target vehicle without corner cutoff.

At its distal end, the telescopic arm 2005 is attached to radiation source 2006 and is deployed from boom 2007, once rotated into desired scanning positions. Single boom 2007 allows for source 2006, positioned at the base of the telescopic arm 2005, to rigidly align with detector array 2003.

An array of laser pointers emitting laser radiation is built into the collimator to facilitate proper alignment of the radiation beam with the detectors. In one embodiment, optical triangulation method is used for aligning the plane of the radiation beam with a predefined "zero" or "idealized centerline" of the detector system. Such optical triangulation techniques, as known to a person of ordinary skill in the art, use a source of light such as a laser pointer to define the radiation beam path. These laser pointers are directed to impinge on a predefined "zero" of the detectors. The "zero" of the detectors may be a spot representing the centroid of the detector system or an idealized centerline representing a spatial x-y locus of an ideal fan beam plane intersecting the plane of the detectors substantially orthogonally. In one arrangement, the spatial position of the laser pointers impinging on the detectors is sensed by an array of photo-electric diodes of the detector system that send the corresponding position signals to a computer housed within the trailer. The computer compares the spatial position of the laser pointers with a predefined "zero" of the detector system and sends correction control signals to the source box through the control cable (attached to the boom) for adjustments until the laser pointers are reasonably lined-up with the detector system.

Radiation source box 2006, attached to telescopic arm 2005, emits penetrating radiation beam 2008 having a cross-section of a particular shape. Several embodiments for the radiation source, but not limited to such embodiments, are described in further detail throughout the specification and will not be described herein. The more rigid alignment of radiation source 2006 with detector array 2003 permits the scanning system of the present invention to operate with a narrower beam width and a lower radiation level. Positioning source 2006 at the base of telescopic arm 2005 also permits a larger field of view relative to the conventional systems having the source on the vehicle. Also, since radiation source 2006 is suspended on the distal end of boom 2007, it can extend as low as six inches off of floor level, shown as 2009, and can provide the under-carriage view 2010 of OUI 2011.

Optionally, boom 2007 deploys and permits detector array 2003 and radiation source box 2006 to extend outward, preferably resting at an angle of about 10 degrees relative to the plane perpendicular to OUI 2011. This permits for easy viewing of dense material and hidden compartments (not shown). The heaviest material in cargo is usually located at the bottom floor of the truck. For example, in one particular embodiment, a linear accelerator (LINAC) is employed. The zero degree center point of the beam is the strongest portion of the beam. In order to capture scans of the floor level of the truck, the radiation source beam is positioned to orientate 15 degrees downward to detect materials in the undercarriage and then 30 degrees upward to detect the higher portions of the load. This ensures that the strongest X-rays (at the zero degree position or, center of the X-ray tube) are oriented at the floor level of the truck, which is critical to the performance of the system as the densest and most difficult portion of a truck to image is the floor level.

Optionally, boom 2007 deploys and permits detector array 2003 and radiation source box 2006 to scan at various heights. In one embodiment, boom 2007, and thus radiation source box 2006, is positioned to scan at standard truck height. In another embodiment, boom 2007, and thus radiation source box 2006, is set at a position closer to the ground, and is suitable for scanning automobiles. It should be noted that the boom structure 2007, radiation source 2006, and detector array 2003 on the same single boom can be positioned at any height without the need for source and detector array realignment.

During the scanning operation, radiation source 2006 and detector array 2003 are activated and the scanning trailer is driven over the OUI, such that the objects get positioned between the trailer and radiation source 2006. In a preferred embodiment, during the scanning operation, the source and detectors remain stationary and aligned with respect to each other while mobilized and passed over the OUI. In a preferred embodiment, the motion of the scanner is kept steady and at a constant velocity. Since, irregularities in the motion of the vehicle may result in distortions in the scanned image, the motion is preferably made as regular, even and constant as feasible using known control systems such as by engaging the trailer motor in "auto speed" mode. As described in greater detail below, the scanning system is manipulated via a closed loop method to automatically correct images for the different speeds of operation of the scanning trailer. Such speed control system is a combination of mechanical, electrical, and software design.

Figure 21:
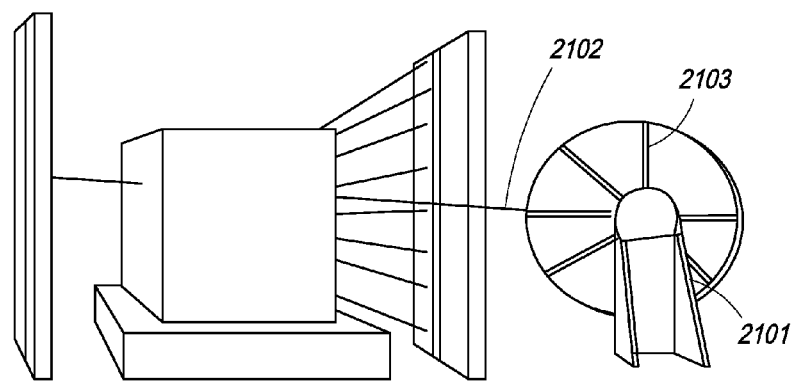
FIG. 21 depicts the rotating collimation wheel employed in the scanning system of the present invention.

Since the source and detector remain in a relative stationary and fixed position during the scanning process, collimation can be adjusted to an advantageous minimum such that the fan beam emerging out of the collimator just covers the detectors. The collimation mechanism employed is preferably a rotating wheel or any other suitable mechanism as known to the person of ordinary skilled in the art. Referring to FIG. 21, a rotating collimation wheel of one embodiment of the present invention is depicted. Rotating wheel 2101 is used to develop pencil beam 2102, which passes through the object. A series of tubular collimators 2103 are distributed as spokes on rotating wheel 2101. Cross-section of pencil beam 2102 is substantially rectangular, but is not limited to such configurations. The dimensions of pencil beam 2102 typically define the scatter image resolution, which may be obtained with the system.

As known in the art, X-ray scanning operates on the principle that, as X-rays pass through objects, the radiation gets attenuated, absorbed, and/or deflected owing to a number of different physical phenomena that are indicative of the nature of the material being scanned. In particular, scattering occurs when the original X-ray hits an object and is then deflected from its original path through an angle. These scatter radiations are non-directional and proportional to the total energy delivered in beam path. A narrowly collimated beam will keep the overall radiation dose minimal and therefore also reduce the amount of scatter radiation in the area surrounding the scanner, thereby reducing the "exclusion zone".

During deployment the inspection trailer is driven to the inspection site and the radiation source and detector booms are positioned. Because the trailer moves over the OUI, it does not need to be positioned strategically to allow for high throughput. Rather, the trailer may be driven over any OUI, located anywhere, given that there is space for the inspection trailer to pass without disrupting port activities. Another aspect that may influence the decision of positioning the trailer could be the availability of a large enough area, called the "exclusion zone", around the scanner system. The exclusion zone is an area around the scanner in which general public are not authorized to enter due to the possibility of their getting exposed to doses of radiations scattered during the scanning process. The exclusion area is dependent upon the magnitude of current setting the intensity of the radiation source.

Figure 22:
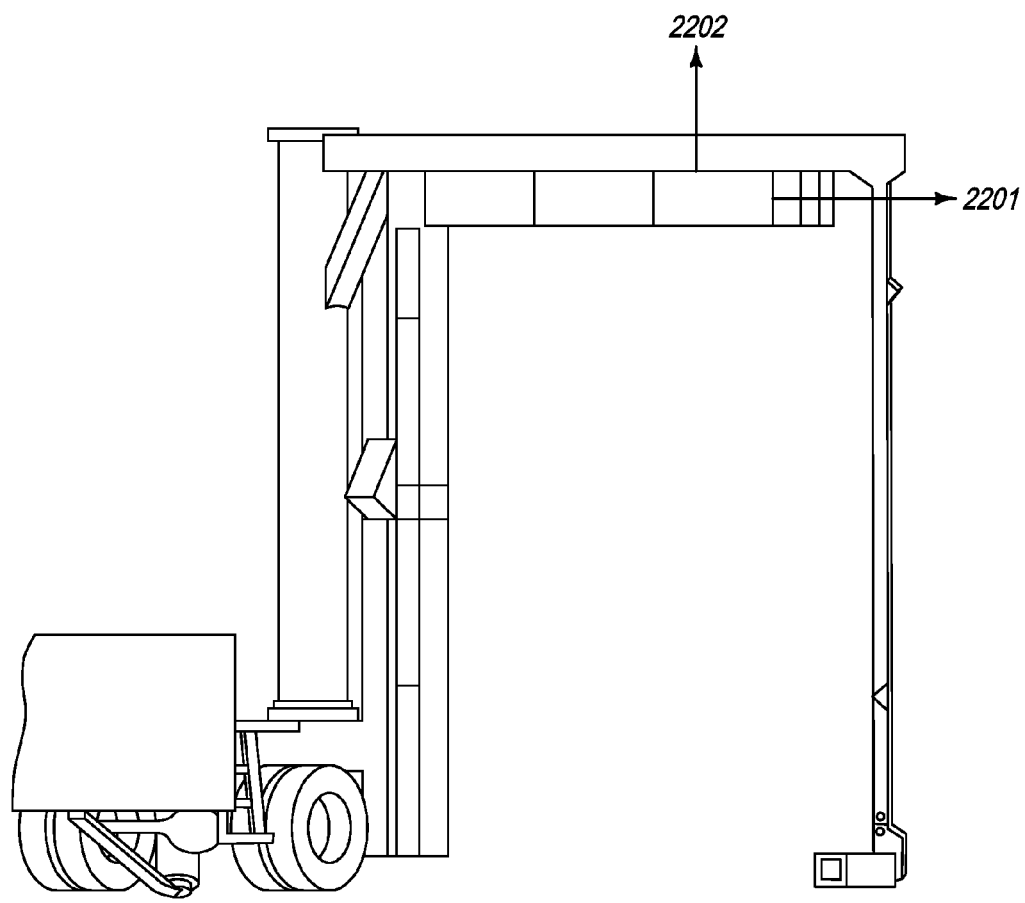
FIG. 22 illustrates a preferred embodiment of the detector array as employed in the single boom cargo scanning system of the present invention.

FIG. 22 illustrates a preferred embodiment of the detector array 2201 as employed in the single boom cargo scanning system of the present invention. The detectors 2202 may be formed by a stack of crystals that generate analog signals when X-rays impinge upon them, with the signal strength proportional to the amount of beam attenuation in the OUI. In one embodiment, the X-ray beam detector arrangement consists of a linear array of solid-state detectors of the crystal-diode type. A typical arrangement uses cadmium tungstate scintillating crystals to absorb the X-rays transmitted through the OUI and to convert the absorbed X-rays into photons of visible light. Crystals such as bismuth germinate, sodium iodide or other suitable crystals may be alternatively used as known to a person of ordinary skill in the art. The crystals can be directly coupled to a suitable detector, such as a photo-diode or photo-multiplier. The detector photodiodes could be linearly arranged, which through unity-gain devices, provide advantages over photo-multipliers in terms of operating range, linearity and detector-to-detector matching. In another embodiment, an area detector is used as an alternative to linear array detectors. Such an area detector could be a scintillating strip, such as cesium iodide or other materials known in the art, viewed by a suitable camera or optically coupled to a charge-coupled device (CCD).

Figure 23:
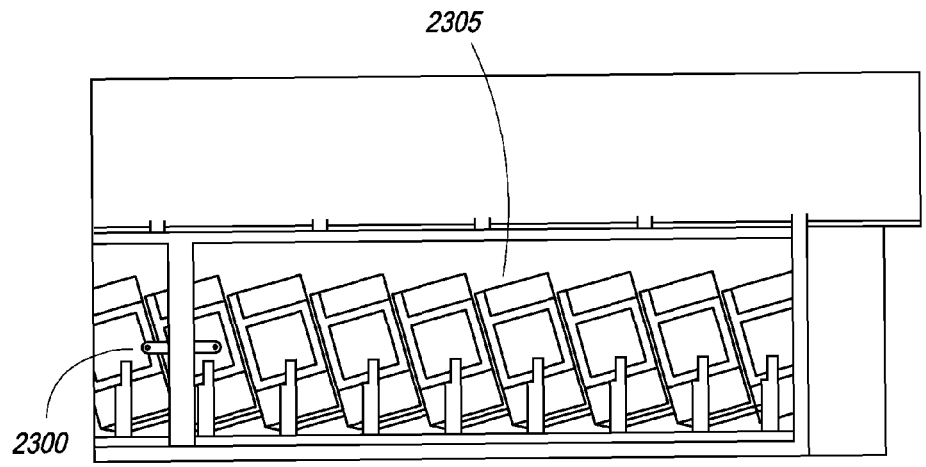
FIG. 23 is a detailed illustration of one embodiment of the detectors employed in the detector array shown in FIG. 10.

FIG. 23 is a detailed illustration of one preferred embodiment of the detectors 2300 employed in the detector array 2305, as shown in FIG. 22. The detectors are preferably angled at 90 degrees relative to the radiation source focal point. The radiation scattered from the radiation source beam is detected by the strategically positioned detectors, thus improving image quality.

Figure 24:
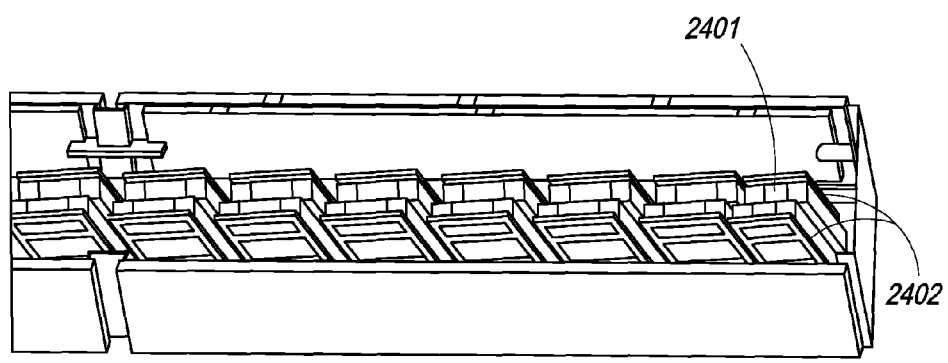
FIG. 24 is a detailed illustration of another embodiment of the detectors employed in the detector array shown in FIG. 10, where the detectors are arranged in a dual row.

FIG. 24 is a detailed illustration of another preferred embodiment of the detectors employed in the detector array shown in FIG. 22, where the detectors are arranged in a dual row. Detector array 2401 preferably comprises a dual row of detectors 2402 that are blended together in an interlacing fashion to allow better resolution using a suitable algorithm. The focus algorithm provides automatic means to combine the images resulting from the dual row of detectors 2402, which are at half-detector offset from each other, into a single row allowing for double resolution compared to a single row of detectors. This blending method eliminates jagged edges in the resultant images from the use of the two detector rows 2402.

At any point in time when the radiation source is on, the detectors are snapshots of the radiation beam attenuation in the OUI for a particular "slice" of the OUI. Each slice is a beam density measurement, where the density depends upon beam attenuation through the OUI. The radiation detectors convert the lateral radiation profile of the OUI into electrical signals that are processed in an image processing system, housed in the inspection trailer, while the OUI is being conducted past the source and the radiation detector.

The X-ray image processing and control system, in an exemplary embodiment, comprises computer and storage systems which record the detector snapshots and software to merge them together to form an X-ray image of the vehicle which may further be plotted on a screen or on other media. The X-ray image is viewed or automatically analyzed by OUI acquisition system such as a CRT or monitor that displays the X-ray image of the vehicle to an operator/analyst. Alternatively, the OUI acquisition systems may be a database of X-ray images of desired targets, such as automobiles, bricks or other shapes that can be compared with features in the image. As a result of this imaging, only articles that were not contained in the reference image of the container or vehicle are selectively displayed to an operator/analyst. This makes it easier to locate articles that do not correspond to a reference condition of the container or vehicle, and then to conduct a physical inspection of those articles. Also, for high-resolution applications, the electronics used to read out the detector signals may typically feature auto-zeroed, double-correlated sampling to achieve ultra-stable zero drift and low-offset-noise data acquisition. Automatic gain ranging may be used to accommodate the wide attenuation ranges that can be encountered with large containers and vehicles.

Figure 25:
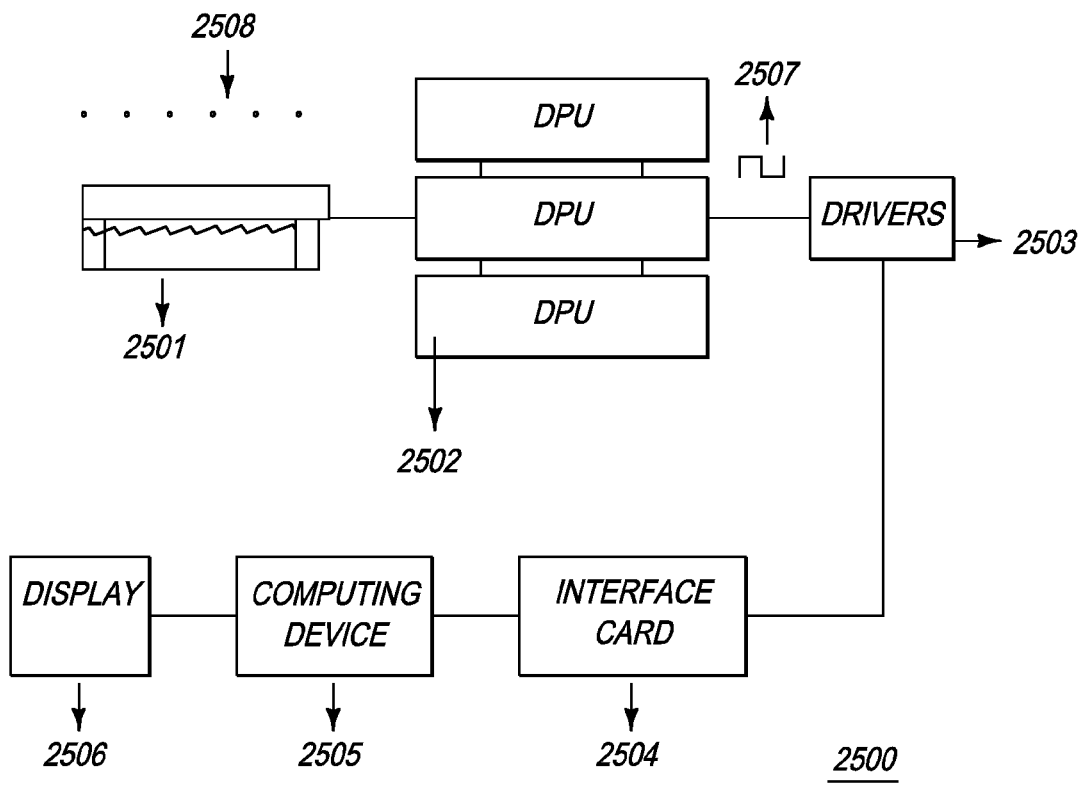
FIG. 25 is a block diagram of an exemplary display and processing unit of the single boom cargo scanning system of the present invention.

FIG. 25 is a block diagram of an exemplary X-ray image processing and display unit of the single boom cargo scanning system of the present invention. X-ray image display and processing unit 2500 includes detectors 2501 coupled through data processing units (DPU) 2502, drivers 2503, interface card 2504 and computing device 2505. Computing device 2505 processes discrete photo current integration information received from the detectors 2501 via interface card 2504, which is attached to computing device 2505. Display device 2506, attached to computing device 2505, renders the image of the contents of the target object upon receiving information from computing device 2505. The detector array includes a plurality of detectors. The detectors 2501 are coupled in groups of data processing circuits (not shown). It is preferred that three groups of detectors 2501 are employed, wherein the number of detectors 2501 in use is dependent upon the height of the OUI (not shown), and the resolution (i.e. number of pixels) of the image desired. In a preferred configuration, three data processing units 2502 are coupled to line driver 2503, which is coupled to network interface 2504. Interface 2504, such as but not limited to RS-485, is embodied on a circuit card located within computing device 2505.

Computing device 2505 is preferably a microprocessor based personal computer system and operates under the control of a software system. Computing device 2505 thus receives detector pulses 2507 from each of the data processing units 2502, in response to the detection of individual photons 2508 by the detectors. The software system processes the incoming detector pulses 2507, evaluates their relative amplitudes (i.e. energies), and generates a radiographic image-like display output signal, which is coupled to the graphical display device 2506, thus generating a graphical representation of the densities within the OUI.

The present invention generates a graphical representation, i.e., an image, of the densities of the contents of the vehicle under inspection. This allows for easy visual interpretation of the results of the scanning of the OUI.

Advantageously, the preferred software system also causes the display of a reference image simultaneously with the image generated in response to the vehicle under inspection, so that an operator of the present embodiment can easily make a visual comparison between what an object of the type being inspected should "look like", and what the OUI actually "looks like". Such "side-by-side" inspection further simplifies the detection of contraband using the present embodiment.

The vertical linear array configuration of the detector array is designed to provide a resolution of grid points spaced approximately every 5 cm along the length and about 4.3 cm along the height of the target OUI. This resolution is adequate to achieve a detectability limit of less than half a kilogram of contraband per 4.3 cm by 5 cm gridpoint (or pixel). The pixel size can be easily varied by appropriately selecting the location of the radiation source and the detectors within the detector array, and by varying the distance between inspections points longitudinally (via choice of counting interval and scan speed along the length of the target vehicle). A suitable algorithm implements a correction that takes into account the speed of the scanning trailer under motion, the scanning rate (i.e., number of lines scanned per second), detector size, and distance between the detectors.

In one embodiment, a closed loop method is employed to automatically correct images for the varying speeds of operation of the scanning system. The speed control system is a function of mechanical, electrical, and software components of the scanning system of the present invention.

Figure 26:
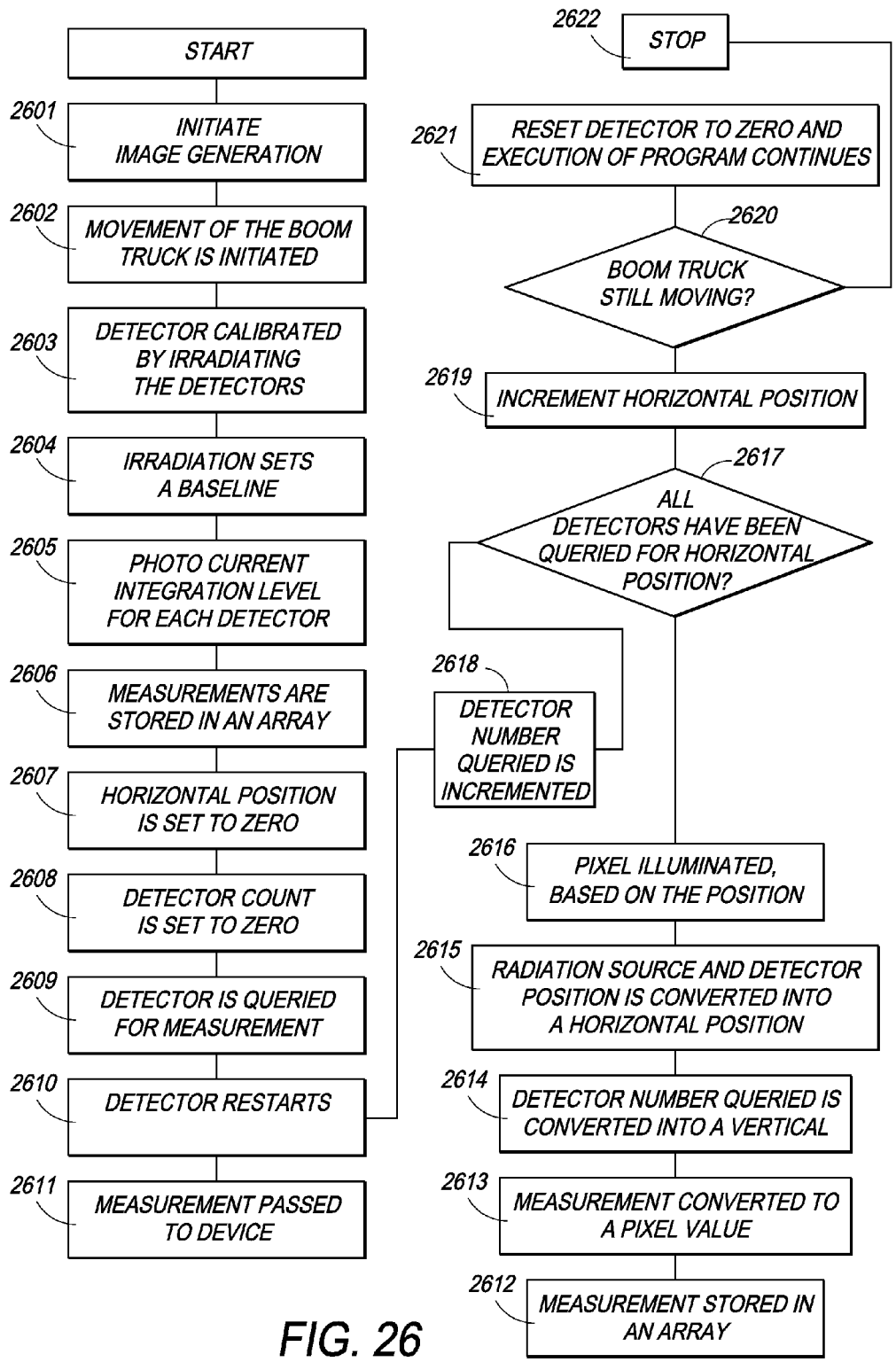
FIG. 26 is a flowchart depicting the operational steps of the single boom cargo scanning system of the present invention upon execution of an image generation program.

Referring to FIG. 26, a flow chart depicts the operational steps of the single boom cargo scanning system of the present invention once the image generation program is executed. In step 2601, the single boom scanning system of the present invention initiates image generation. In step 2602, movement of the trailer containing the single boom begins. In another embodiment, where the OUI is optionally driven underneath and through the self-contained inspection system, start-sensors may be strategically placed to allow an imaging and control system, located within the inspection trailer, to determine that the OUI cab, in the case of a vehicle, has passed the area of beam and the vehicle to be inspected is about to enter the X-ray beam position. Thus, as soon as the vehicle to be inspected trips the start-sensors, the radiation source is activated to emit a substantially planar fan-shaped or conical beam for the duration of the pass) that is suitably collimated for sharpness and made to irradiate substantially perpendicular to the path of the vehicle.

In step 2603, the detectors are calibrated by irradiation with the radiation source at a point along the track prior to the radiation source arm and detector array arm reaching the OUI. In other words, calibration occurs before the OUI is interposed between the detector array and the radiation source. The irradiation of the detector array sets a baseline, in step 2604 of radiation (or "white" photo current integration level) analogous to a density in the OUI approximately zero and a maximum photo current integration level. In step 2605, three photo current integration measurements are preferably made in this manner for each detector. In step 2606, measurements are arranged for each detector and stored in an array having a white level element for each detector.

In step 2607, the horizontal position is set to zero. The horizontal position corresponds to a position along the scanning track, randomly selected, at which density measurements are taken for the first time. This horizontal position should be at a point before the OUI is interposed between the detector array and the radiation source. In step 2608, the detector measurement is set to zero, corresponding to the first detector in the detector array to be queried for a photo current integration level. The detector is queried in step 2609 for a photo current integration level and is instructed to restart measurement. In step 2610, the detector restarts measurement in response to the instruction to restart. In step 2611, photo current integration level determined in step 2609 is passed to the measurement device. In step 2612, the level of photo current integration measured is stored in an array and is then converted into a pixel value in step 2613. The conversion is achieved by mapping the amount of photo current integration to a color, for display on the display device. In step 2614, the detector number queried is converted into a vertical position on the screen display. The horizontal position of the radiation source and the detector array along the scanning track is converted to a horizontal position on the screen display in step 2615. Once the vertical and horizontal positions are ascertained, a pixel is illuminated in step 2616 using the color corresponding to the photo current integration level.

In step 2617, a determination is made as to whether all of the detectors in the detector array have been queried for a photo current integration level for the current horizontal position. If all the detectors have not been queried, the detector number to be queried is incremented in step 2618. The image generation program continues by querying the next detector in the detector array for the photo current integration level and by instructing such detector to restart measurement as in step 2610. The image generation program continues executing from this step, as described in detail above.

If all the detectors within the detector array have been queried for the current horizontal position, the horizontal position is incremented in step 2619. In step 2620, a determination is made as to whether or not the radiation source arm and the detector array arm of the single boom scanning trailer are still in motion. If the boom components are still in motion, the detector to be queried is reset to zero and the image generation program continues, as shown in step 2621. If the single boom scanning system has stopped moving, the image generation program is terminated in step 2622.

In another embodiment, the present invention is directed towards a portable inspection system for generating an image representation of target objects using a radiation source, comprising a mobile vehicle; a detector array physically attached to a single, movable boom having a proximal end and a distal end wherein the proximal end is physically attached to a turntable, which is, in turn, physically attached to the mobile vehicle; and at least one source of radiation wherein the radiation source is attached to the distal end of the boom and adjustable to a desired scanning height, wherein the image is generated by introducing the target objects in between the radiation source and the detector array, exposing the objects to radiation, and detecting radiation.

The present invention provides for an inspection system that can easily be transported in a compact stowed configuration. The compact configuration lends a low center of gravity for better stability of the inspection system during road transport, as there is often a need for driving the inspection system in hilly areas, border crossings, and steep mountainous areas. In addition, due to its low profile stowed configuration, the inspection system of the present invention is capable of being transported by cargo and/or military aircraft, thus facilitating rapid delivery to outlying areas.

Thus, the system of the present invention is advantageous, among other benefits, in that it provides a highly compact stowed configuration with low center of gravity for stability; a sturdy deployed configuration with radiation source and detectors readily aligned; a selectable scan angle position, and it can be converted from a stowed configuration to a deployed and operational configuration in areas having limited horizontal and vertical clearance. The inspection methods and systems of the present invention are mobile, rapidly deployable, and capable of scanning a wide variety of receptacles cost-effectively and accurately, with rigidity, ease of use, and a wider field of vision.

While reference will be made to FIGS. 27A, 27B, 27C, 27D, 27E, 27F, 27G, 27H to describe the features of the inspection system of the present invention, reference will simultaneously be made to the flow chart of FIG. 28, which describes the operational steps of bringing the inspection system from a stowed configuration to a deployed and operational configuration.

Figure 27A:
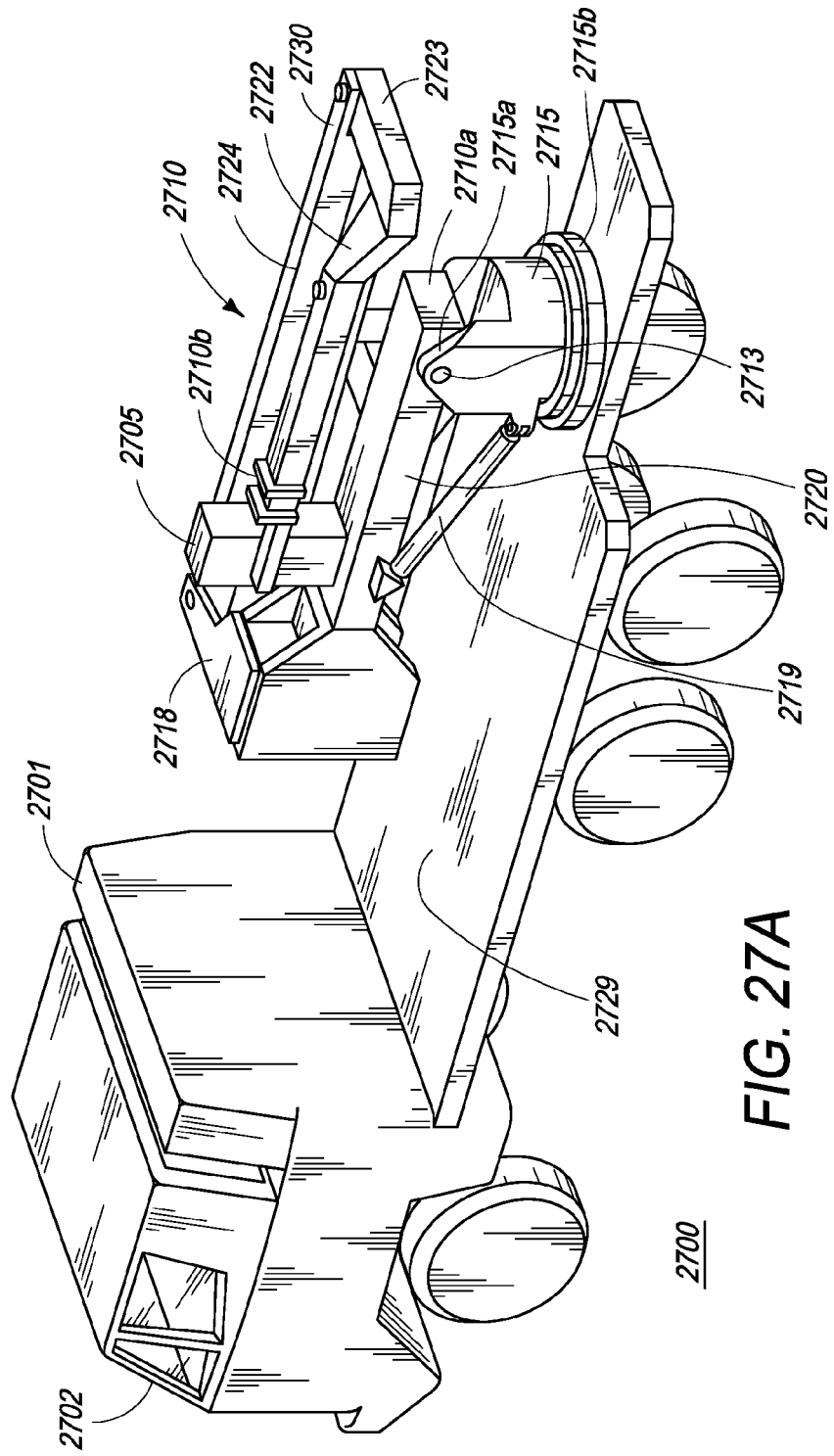
FIG. 27A is an illustration of one embodiment of a single boom system employed in the self-contained mobile inspection system of the present invention, further comprising a turn-table and in a stowed configuration.

FIG. 27A is an illustration of a single boom system employed in the self-contained mobile inspection system of the present invention in a stowed configuration, which, in one embodiment, further comprises a turntable 2715. The turntable, in one embodiment, and as described in greater detail below, is employed to minimize the horizontal or vertical space clearance required during system deployment. In another embodiment, the turntable 2715 is employed to allow the operator to select a scanning side, such as driver's side or passenger's side of a rig or tractor trailer. Further, in yet another embodiment, the use of a turntable 2715 allows for the operator to select a desired scan angle position, which is preferably selected by considering several factors, including the size of the object under inspection (OUI), the shape of the OUI, the position of the OUI, and the operator's preferred viewing angle.

Referring now to FIG. 27A, the self-contained inspection system 2700 of the present invention comprises, in one embodiment, an inspection module in the form of a rig/tractor trailer 2701, capable of being driven to its intended operating site. In one embodiment, the vehicular portion of the system and the inspection module portion of the system may be integrated into a single mobile structure.

The integrated modular mobile structure serves as a support and carrier structure for at least one source of electromagnetic radiation 2705, which is capable of emitting radiation having at least one energy level. In one embodiment, the at least one source of radiation 2705 is capable of emitting radiation in two different energy levels. In another embodiment, the inspection or scanning module 2700 can provide support for two discrete sources of radiation 2705, wherein the discrete sources of radiation can be of different energies.

Now referring back to FIG. 27A, self-contained inspection system 2700 further comprises a boom structure 2710, having a proximal end 2710a (close to the rig platform 2729) and a distal end 2710b (the extendable portion of the boom). Radiation source 2705 is securely attached to a portion of the distal end 2710b of boom 2710. In one embodiment, proximal end 2710a of boom 2710 is movably attached, via pivot 2713, to a top portion 2715a of turntable 2715; boom 2710 can elevated via rotation about pivot 2713. In addition, in one embodiment, a bottom portion 2715b of turntable 2715 is integrated into the rig/tractor trailer portion 2701 of self-contained mobile inspection system 2700, and more specifically into the surface of the back of the rig 2729. Boom 2710 additionally houses an array of detectors 2730, described in greater detail below.

It should be noted that boom 2710 and turntable 2715 are, in one embodiment, installed and located in the back of trailer 2701 to minimize radiation dosage to driver in trailer cab 2702. Trailer 2701 also houses an operator/analyst cabin including computer and imaging equipment along with associated power supplies, air conditioning and power generating equipment (not shown) in accordance with the understanding of a person of ordinary skill in the art of X-ray generation. Depending on conditions, other system elements may be deployed to enable the screening process. Such elements may include surveillance systems such as the closed-circuit television (CCTV) to monitor area around the scanner to control the exclusion zone, a lighting system and a wireless network. The lighting system may be required to facilitate night operation. In a preferred embodiment the analysis of the scanned images of an OUI are done by an analyst seated inside the inspection trailer. However, in another embodiment a separate command center may alternatively or additionally be located away from the scanner, preferably outside the exclusion zone, where a similar analysis of scanned images may be done. In such an arrangement wireless networks may additionally be needed to transfer data from the scanner system to the command center.

The radiation source box 2705 is located on the same single boom 2710 as the detection array 2730. Thus, while source box 2705 is located opposite the detector array 2730 at a distance that is suitable to allow Object under Inspection ("OUI") to pass in the area (not shown) between the source 2705 and detector array 2730 during the scanning process, it is located on the same boom 2710 to eliminate the need for alignment. In one embodiment, the radiation source 2705 is an X-ray generator. In yet another embodiment, the radiation source is a linear accelerator (LINAC). If the X-ray generator or LINAC is mounted on the same single boom as the detector arrays, the need for sophisticated alignment systems each time the system is deployed is eliminated. Thus, the radiation source and detectors are substantially permanently aligned on the same single boom. The feature also allows for scanning at various degrees of offset, again without the need to realign the LINAC or X-ray generator and detectors.

The source of radiation includes radio-isotopic source, an X-ray tube, LINAC or any other source known in the art capable of producing beam flux and energy sufficiently high to direct a beam to traverse the space through an OUI to detectors at the other side. The choice of source type and its intensity and energy depends upon the sensitivity of the detectors, the radiographic density of the cargo in the space between the source and detectors, radiation safety considerations, and operational requirements, such as the inspection speed. The system of the present invention could employ source-based systems, for example, cobalt-60 or cesium-137 and further employ the required photomultiplier tubes (PMT) as detectors. If a linear accelerator (LINAC) is optionally employed, then photodiodes and crystals are used in the detector. One of ordinary skill in the art would appreciate how to select a radiation source type, depending upon his or her inspection requirements.

In one embodiment, where the OUI is a large sized container or car that highly attenuates the X-ray beam, the radiation could be from an X-ray tube operating at a voltage in substantial excess of 200 keV, and may operate in varying regions, including 450 keV, 3 MeV, 4.5 MeV, and even, but not limited to 6 MeV.

In one embodiment, the present invention employs dual source-based systems and further employs the required photomultiplier tubes as detectors. In one embodiment, $^{60}$Co is used as a first gamma ray source and has a high specific activity of the order of 11.1 TBq (300 Ci) and a linear dimension of the active area of 6 mm. In one embodiment, the second gamma ray source is a 1.0, 1.6 or 2.0 Curie shuttered mono-energetic source of $^{137}$Cs gamma rays, having a 662 keV energy.

In another embodiment, a nearly mono-energetic $^{60}$Co gamma ray source is used, which is capable of emitting photons at two distinct energy levels, more specifically, 1170 and 1339 KeV. In one embodiment, the gamma rays emitted from the $^{60}$Co source are collimated by their slits to form a thin fan-shaped beam with a horizontal field angle of 0.1° and a vertical field angle of 80°.

In one embodiment, boom 2710 is capable of being folded into trailer 2701 in a "stowed" configuration or folded out from trailer 2701 in a "deployed" configuration, on either the driver or passenger side. In one embodiment, the turntable 2715 can be rotated from a stowed scan angle position of 0° through 360°, however, preferred deployment rotation angles range from between 80° and 100° or range from between 260° and 280°, as the boom 2710 can only be unfolded when positioned at these angles.

In one embodiment, in order to minimize the horizontal operational space required during deployment, the boom is first lifted vertically into an upright position, substantially 90 degrees, and subsequently rotated about the turntable to the desired angle of deployment. Thereafter, the detector box and radiation source portions are unfolded. In an alternative embodiment, in order to minimize the vertical operational space required during deployment, the boom is initially lifted to an angle of substantially 45 degrees, and subsequently rotated on the turntable to the desired angle of deployment. Thereafter, the detector box and radiation source positions are unfolded.

Both embodiments are described in greater detail below with respect to corresponding figures. It should be noted herein, although described in greater detail below, that vertical motion of the source is effectuated using a telescopic extension driven by a hydraulic cylinder. The other deployment motions described below occur about hinge points driven by hydraulic cylinders.

Referring to FIG. 27A, when in a stowed position, one embodiment of the present invention includes a boom structure 2710 comprising a first section 2720, a first connecting member 2718, a second section 2724, a second connecting member 2723, and a third section 2722. Radiation source 2705 is connected to the third section 2722 at distal end 2710b of boom 2710. The first section 2720, in a first plane, is substantially parallel to the surface of the back of the rig 2729 and physically connected to the turntable 2715 by a pivot 2713 at the proximal end 2710a and by hydraulic connectors 2719. The first section 2720 is substantially perpendicular to the first connecting member 2718, both of which are in the first plane. The second section 2724 is also substantially perpendicular to first connecting member 2718, both in the first plane, and, further, second section 2724 is parallel to the first section 2720. The second section 2724 is also substantially perpendicular to the second connecting member 2723, both of which are in the first plane. The second connecting member 2723 is preferably parallel to the first connecting member 2718 and perpendicular to the third section 2722, which is in the first plane and parallel to both the first section 2720 and second section 2724.

Figure 27B:
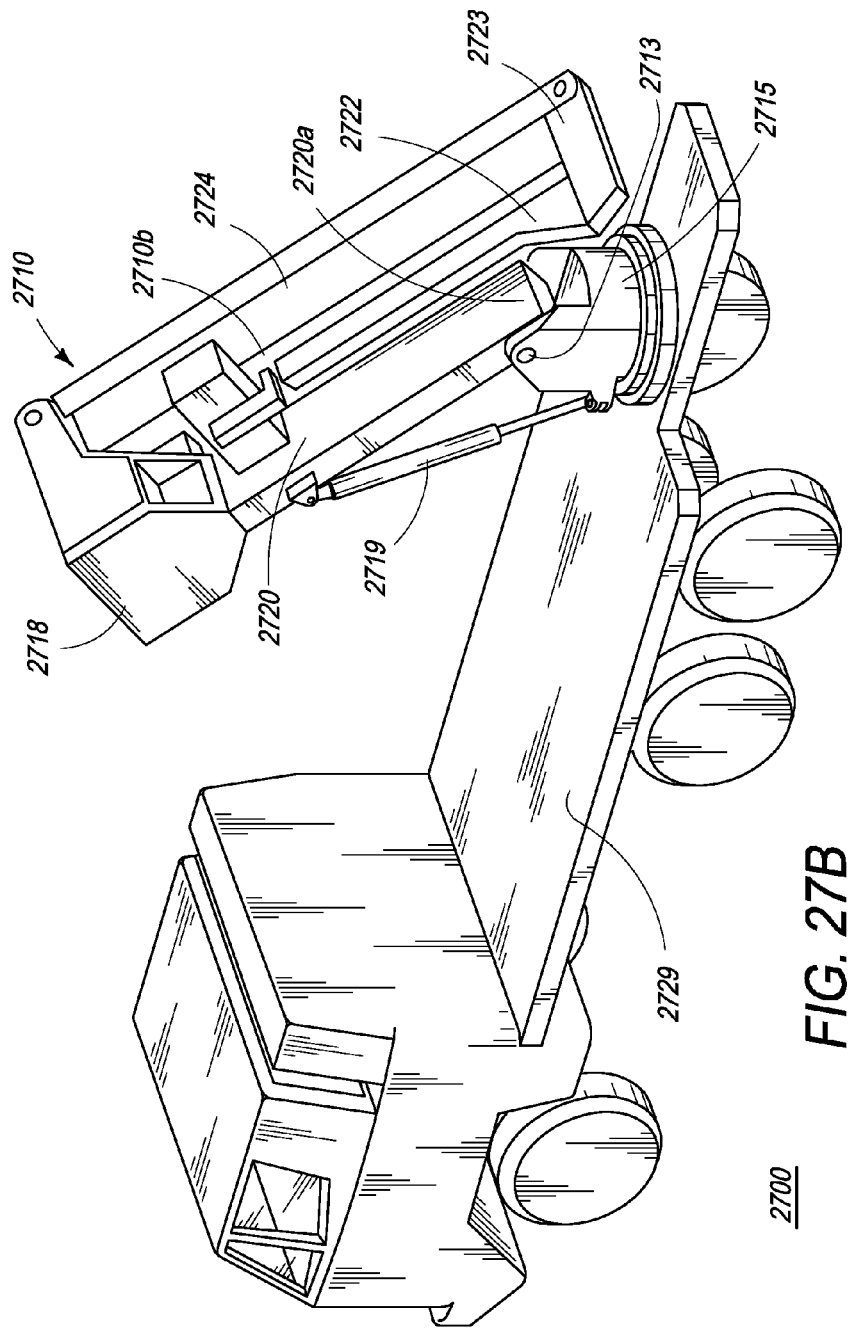
FIG. 27B is an illustration of one embodiment of a single boom system employed in the self-contained mobile inspection system of the present invention, in a partially deployed configuration.

FIG. 27B is an illustration of one embodiment of a single boom system employed in the self-contained mobile inspection system of the present invention, in a partially deployed configuration. As shown in FIG. 27B, and simultaneously referring to FIG. 28, in step 2850, boom 2710 is vertically elevated in its entirety, by rotation about pivot point 2713 by use of a suitable hydraulic system known to a person having ordinary skill in the art. One exemplary hydraulic system for unfolding the system components comprises a reversible electrical motor to drive a hydraulic pump that in turn provides hydraulic fluid under pressure to a double acting hydraulic actuator attached to the trailer. When the hydraulic actuator is required to unfold the boom, pressurized hydraulic fluid is pumped into the chamber, engaging hydraulic connectors 2719, in this case a piston, to move, and in turn, lifts or unfolds the boom. Once the boom 2710 is elevated to an acceptable angle, a similar arrangement can be used to deploy the remaining boom components, including detector panels.

In one embodiment, as shown in FIG. 27B, in order to minimize vertical operational space requirements, in step 2850, boom 2710 is lifted such that it is upright and forms a substantially 45° angle with the surface of the back of the rig 2729. Thus, when in a partially deployed position, in an embodiment that minimizes vertical space requirements, first section 2720 of boom structure 2710 is in a first plane, positioned at a substantially 45 degree angle to the surface of the back of the rig 2729, and physically, yet movably, connected to the turntable 2715 by a pivot 2713 at the proximal end 2720a and by hydraulic connectors 2719. The first section 2720 is substantially perpendicular to the first connecting member 2718, which is also in the first plane. The second section 2724 is also substantially perpendicular to first connecting member 2718, both of which are also in the first plane, and, further, is parallel to the first section 2720. The second section 2724 is also substantially perpendicular to the second connecting member 2723, which is also in the first plane. The second connecting member 2723 is preferably parallel to the first connecting member 2718 and perpendicular to the third section 2722, which is in the first plane and parallel to both the first section 2720 and second section 2724.

In an alternate embodiment (not shown), in order to minimize horizontal operational space requirements, in step 2850, boom 2710 is first elevated such that it is upright and forms a substantially 90° angle with the surface of the back of the rig 2729. Thereafter, a scan angle position is chosen, as shown and described with respect to FIGS. 27C and 27D and remaining components are deployed, as shown in FIGS. 27E, 27F, 27G, 27H. It should be understood by those of ordinary skill in the art that the boom 2710 can first be elevated to the full 90 degree angle with respect to the surface of the back of the rig 2729 and then rotated to the desired scan angle position. Thus, the invention will only be described with respect to the configuration shown in FIG. 27B, where the boom is first partially elevated to a 45 degree angle position with respect to the surface of the back of the rig 2729.

Figure 27C:
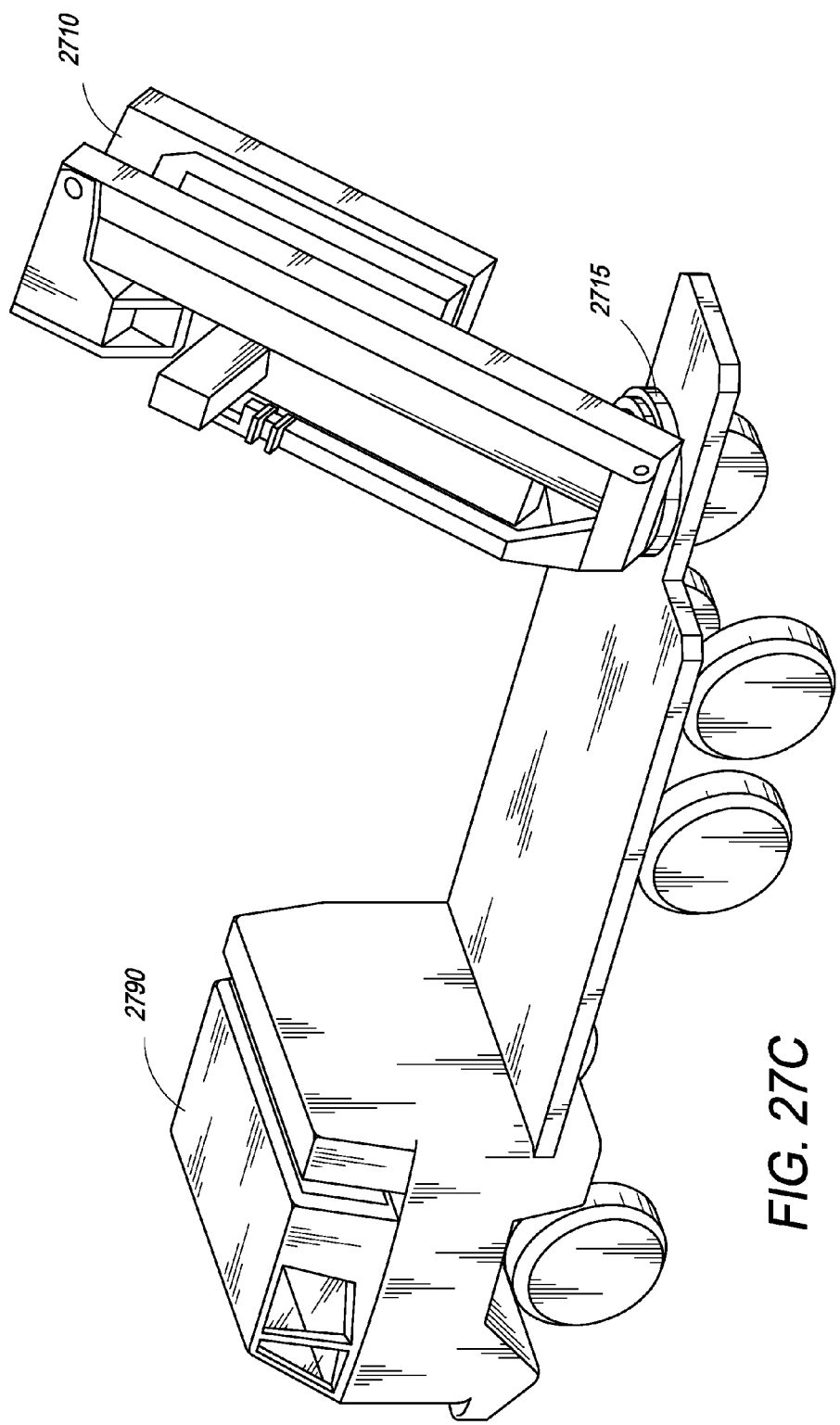
FIG. 27C is an illustration of one embodiment of a single boom system employed in the self-contained mobile inspection system of the present invention, in a partially deployed configuration.
Figure 27D:
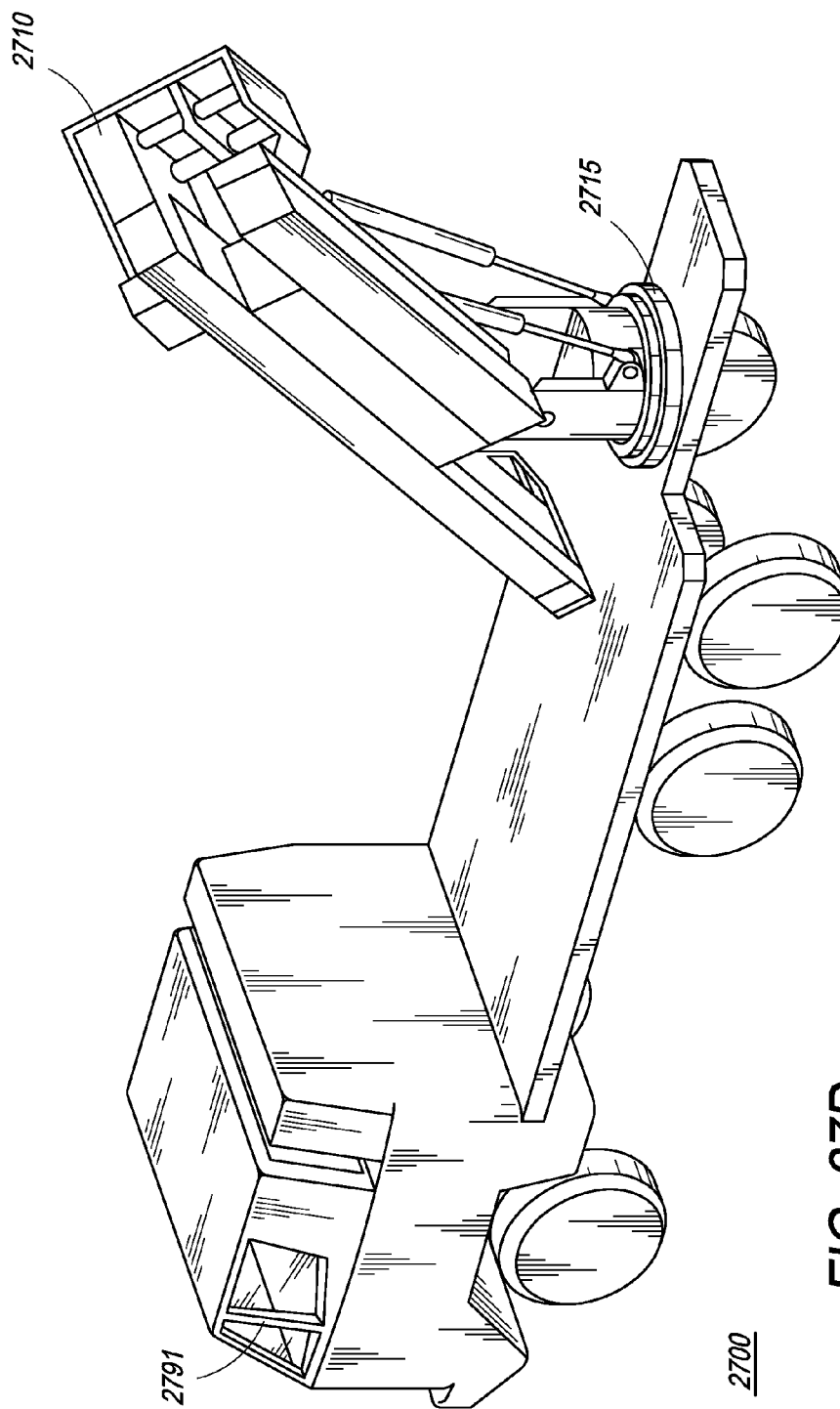
FIG. 27D is an illustration of one embodiment of a single boom system employed in the self-contained mobile inspection system of the present invention, in a partially deployed configuration.

In another embodiment, turn-table 2715 is employed to allow the operator to select a scanning side, such as driver's side or passenger's side. Further, in yet another embodiment, the use of turn-table 2715 allows for the operator to select a desired scan angle position, which is preferably selected by considering several factors, including the size of the object under inspection (OUI), the shape of the OUI, the position of the OUI, and the operator's preferred viewing angle. As the scan angle increases, the overall opening through which the OUI passes decreases. FIGS. 27C and 27D illustrate such embodiments and show how the various boom elements remain in the original configuration, although moving relative to the back surface of the rig, until the proper scan position is established.

FIG. 27C is an illustration of one embodiment of a single boom system employed in the self-contained mobile inspection system of the present invention, in a partially deployed configuration. Also referring to FIG. 28, in step 2855, turn-table 2715 is used to rotate boom 2710. As shown in FIG. 27C, in a first embodiment, turn-table 2715 is employed to rotate boom 2710 (while still folded at its internal pivot points and retaining the configuration described with respect to FIG. 27B), in step 2855, to the passenger side of the truck 2790. In one embodiment, the scan angle is positioned ranging from 260° to 280° when deployed on the passenger side 2790 of the truck. The scan angle position can be adjusted incrementally by 1°.

Referring to FIG. 27D, in a second embodiment, turn-table 2715 is employed to rotate boom 2710 (while still folded at its internal pivot points and retaining the configuration described with respect to FIG. 27B), in step 2855, to the driver side 2791 of the truck. In one embodiment, the scan angle is positioned ranging from 80° to 100° when deployed on the driver side 2791 of the truck. The scan angle position can be adjusted incrementally by 1°.

Figure 27E:
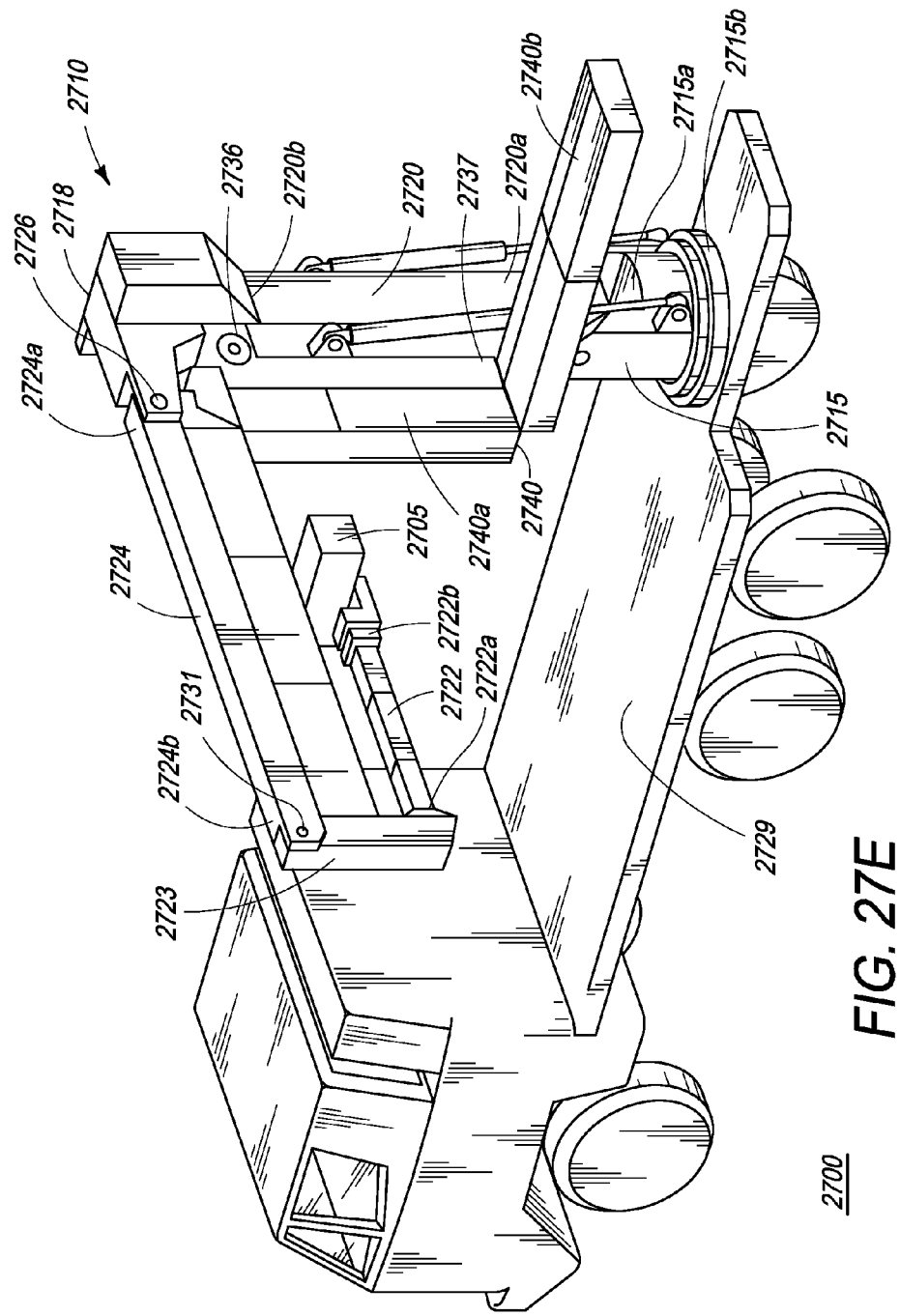
FIG. 27E is an illustration of one embodiment of a single boom system employed in the self-contained mobile inspection system of the present invention, in a partially deployed configuration.

FIG. 27E is an illustration of one embodiment of a single boom system employed in the self-contained mobile inspection system of the present invention, in a partially deployed configuration. Boom 2710 comprises first section or vertical boom arm 2720, having a proximal end 2720a and a distal end 2720b, where the proximal end 2720a is connected to top portion 2715a of turntable 2715 at a pivot point (not shown) and distal end 2720b is connected to a first connecting member 2718. Boom 2710 further comprises a second section 2724, which includes a detector box, and is physically and movably attached, at its proximal end 2724a, to first connecting member 2718, at pivot joint 2726. Distal end 2724b of second section 2724 is connected to a second connecting member 2723, at pivot 2731. Boom 2710 further comprises a third section or source arm 2722, wherein the proximal end 2722a of the source arm 2722 is physically attached to second connecting member 2723 at a pivot point (not shown) and distal end 2722b of third section 2722 is physically attached to radiation source 2705. Boom 2710 further comprises a fourth section 2740, which includes a detector box, and also comprises upper section 2740a and lower section 2740b and is physically and movably attached, at its proximal end or upper section 2740a to first connecting member 2718, at pivot point 2736.

Figure 28:
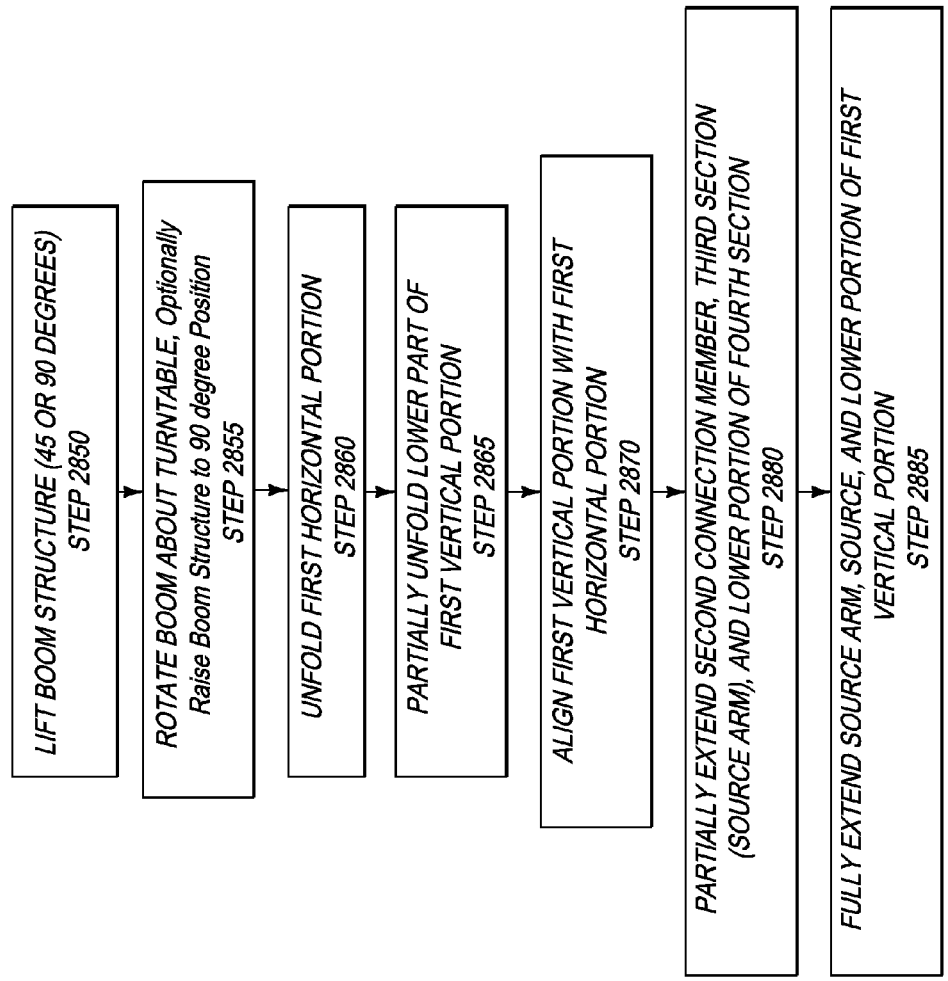
FIG. 28 is a flow chart describing operational steps in bringing the inspection system of the present invention from a stowed configuration to a deployed and operational configuration.

Once turn-table 2715 is completely rotated to either the driver or passenger side, boom 2710 is fully elevated to an angle of 90 degrees with respect to the surface of the back of the rig 2729 and second section 2724 is unfolded about pivot 2726, in step 2860 shown in FIG. 28, such that it comes to rest, or is fully deployed, at an angle of approximately 90 degrees with respect to first section 2720.

While the system is depicted with a predefined set of pivot points, it should be appreciated that any number of pivot points may be used. Although the system is described above with respect to discrete motions about the pivot points, it should be noted herein, and understood by those of ordinary skill in the art, that in order to hasten the stowing and deployment configuration processes, it is possible to perform multiple motions about the pivot points simultaneously.

Thus, in a partially deployed configuration, first section 2720, in a first plane, is at a substantially 90 degree angle to the surface of the back of the rig 2729, and is physically connected to the turntable 2715 by a pivot 2713 at the proximal end 2720a. The first section 2720 is substantially perpendicular to the first connecting member 2718, also in a first plane. The second section 2724, also in a first plane, is connected to first connecting member 2718, and, further, is perpendicular to the first section 2720, once unfolded. The second section 2724 is also substantially perpendicular to the second connecting member 2723, both of which are in the first plane. The second connecting member 2723 is perpendicular to the third section 2722, which is in the first plane and parallel to second section 2724, and perpendicular to first section 2720.

Upper section 2740a of fourth section 2740 is parallel to first section 2720, but in a second plane, as it is offset from the second portion 2724. Lower section 2740b of fourth portion 2740 is partially unfolded about pivot 2737, in step 2865, so that it forms an angle of approximately 90 degrees with respect to upper section 2740a. Thus, lower section 2740b is parallel to the surface of the back of rig 2729. It should be noted that the lower section 2740b is only partially extended at this point to lend stability to the truck.

As described in detail above, the detectors optionally comprise panels that are capable of being folded and easily stored. By forming detectors such that they can fold in a storage configuration, it is possible to produce a compact trailer that can safely, and legally, travel roadways. When unfolded during operation, the detectors assume either a linear or an arched shape. As described above with respect to FIG. 22, the detectors may be formed by a stack of crystals that generate analog signals when X-rays impinge upon them, with the signal strength proportional to the amount of beam attenuation in the OUI. In one embodiment, the X-ray beam detector arrangement consists of a linear array of solid-state detectors of the crystal-diode type. A typical arrangement uses cadmium tungstate scintillating crystals to absorb the X-rays transmitted through the OUI and to convert the absorbed X-rays into photons of visible light. Crystals such as bismuth germinate, sodium iodide or other suitable crystals may be alternatively used as known to a person of ordinary skill in the art. The crystals can be directly coupled to a suitable detector, such as a photodiode or photo-multiplier. The detector photodiodes could be linearly arranged, which through unity-gain devices, provide advantages over photo-multipliers in terms of operating range, linearity and detector-to-detector matching. In another embodiment, an area detector is used as an alternative to linear array detectors. Such an area detector could be a scintillating strip, such as cesium iodide or other materials known in the art, viewed by a suitable camera or optically coupled to a charge-coupled device (CCD).

Thus, as shown in FIG. 27E, in one embodiment, in order to stow the system into a compact and easily relocatable system, the second portion 2724 and fourth portion 2740 are stored, and thus positioned, at an offset relative to one another so that they are initially perpendicular to each other, yet in different planes.

Figure 27F:
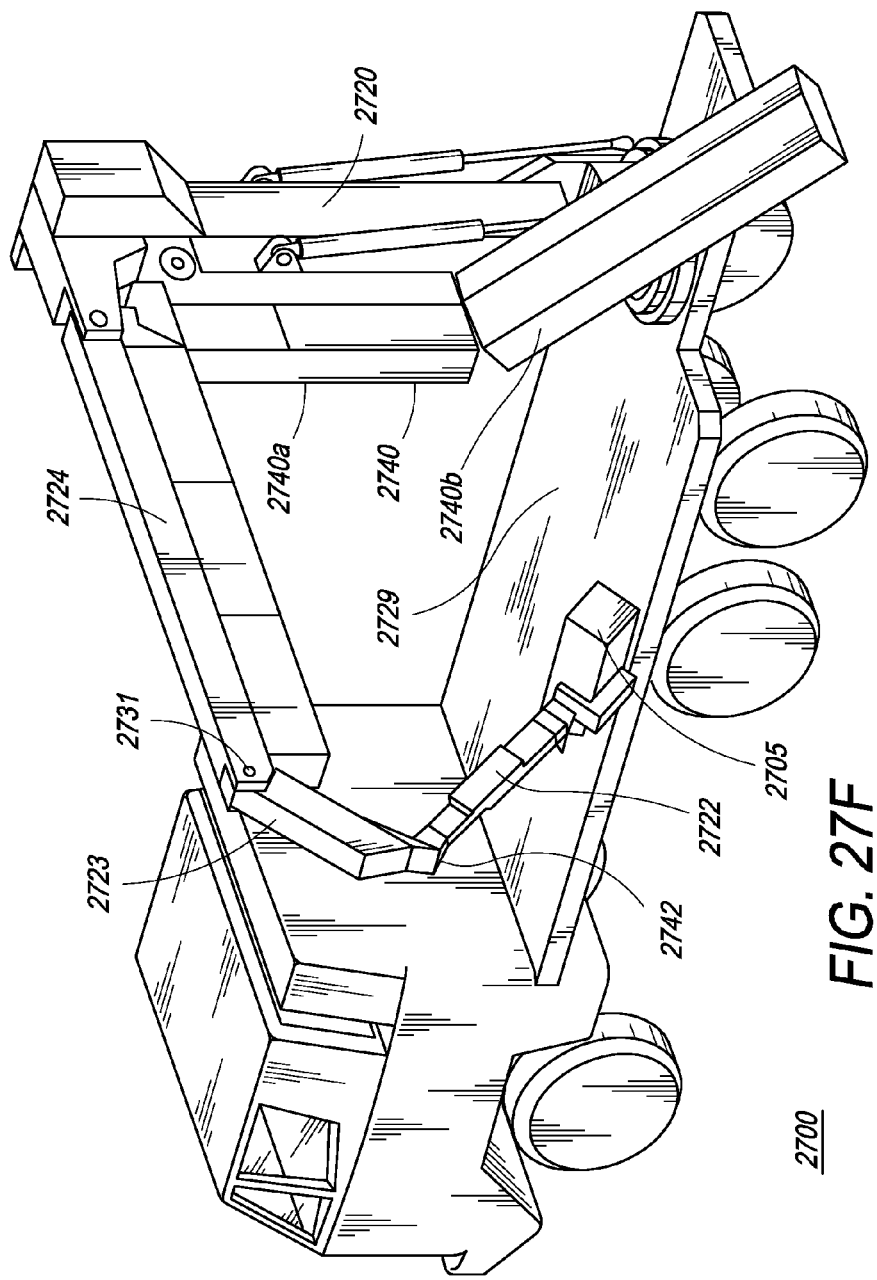
FIG. 27F is an illustration of one embodiment of a single boom system employed in the self-contained mobile inspection system of the present invention, in a partially deployed configuration.

Thus, as shown in FIG. 27F, fourth portion 2740 is shifted in the horizontal direction in step 2870, such that upper section 2740a aligns in the same plane, but is still perpendicular to, second portion 2724. Referring now to FIG. 27F, in addition to the alignment step, second connecting member 2723 is unfolded about pivot point 2731 at second section 2724, and third section 2722 is unfolded at pivot point 2742, in step 2880. Thus, third section 2722 and second connecting member 2723 are still in the same plane as second section 2724, but rest at an angle with respect to second section 2724. In addition, lower section 2740b is again partially extended in step 2880, so that it is no longer parallel to the surface of back of rig 2729, but in an entirely different plane and positioned at an angle of greater than 90 degrees relative to upper portion 2740a, which is parallel to and in the same plane as first section 2720.

Figure 27G:
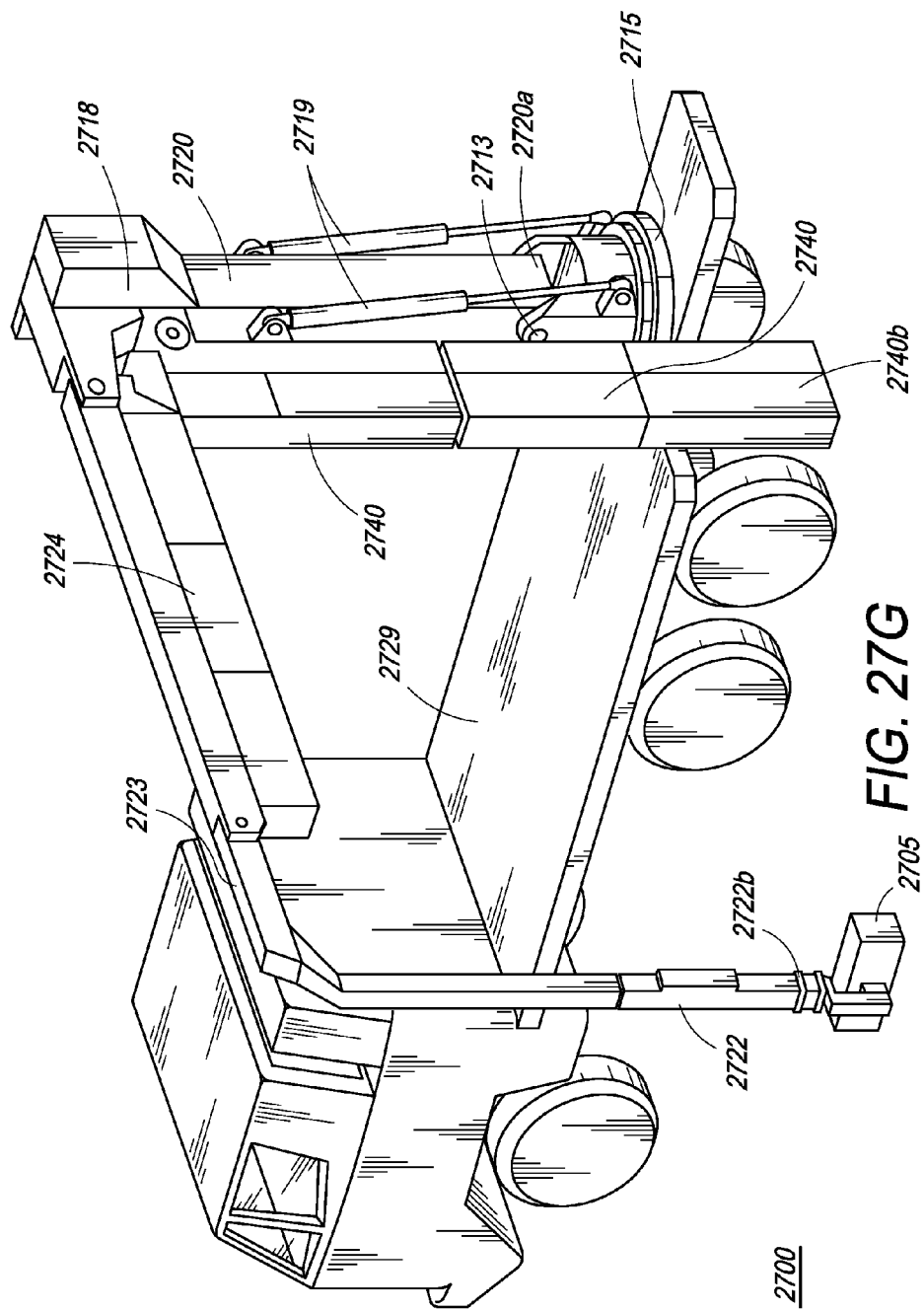
FIG. 27G is an illustration of one embodiment of a single boom system employed in the self-contained mobile inspection system of the present invention, in a fully deployed configuration.

Thereafter, as shown in FIG. 27G, third section 2722 and lower section 2740b of fourth section 2740 are fully extended, in step 2885, such that the boom is in a fully deployed configuration. FIG. 27G is an illustration of one embodiment of a single boom system employed in the self-contained mobile inspection system of the present invention in a fully deployed configuration. In one embodiment, the detector array assumes an approximate inverted "L" shape, since the detectors are contained in second section 2724 and fourth section 2740. The inverted "L" shape detector enables the radiation source to be closer to the target vehicle, thus allowing higher penetration capability, and provides for complete scanning of the target vehicle without corner cutoff.

Referring to FIG. 27G, when in a fully deployed and operational configuration, one embodiment of the present invention includes a boom structure comprising a first section 2720, a first connecting member 2718, a second section 2724, a second connecting member 2723, a third section 2722, and a fourth section 2740. Radiation source 2705 is connected to the distal end 2722b of the third section 2722. The first section 2720, in a first plane, is substantially perpendicular to the surface of the back of the rig 2729 and physically connected to the turntable 2715 by a pivot 2713 at the proximal end 2720a and by hydraulic connectors 2719. The first section 2720 is substantially perpendicular to the first connecting member 2718, both of which are in the first plane, which is perpendicular to the back side of the rig 2729. The second section 2724 is connected to a portion of first connecting member 2718 and, further, second section 2724 is perpendicular to the first section 2720. The second section 2724 is substantially parallel to the second connecting member 2723, both of which are in the first plane. The second connecting member 2723 is preferably perpendicular to the third section 2722, which is in the first plane and parallel to both the first section 2720 and fourth section 2740. Further, fourth section 2740 is perpendicular to and in the same plane as second section 2724.

In one embodiment, the radiation source box 2705 is located on the same single boom as the detector boxes (as described above) eliminating the need for sophisticated alignment systems each time the system is deployed. Thus, the radiation source 2705 is permanently fixed in alignment relative to the detector boom. The radiation source 2705 is located on one side of the boom while the detectors are located on the other. The rotating turn-table boom allows for the source of radiation 2705 to be positioned opposite the area of the boom supporting the detectors. The detectors are preferably angled at 90° relative to the radiation source focal point. The radiation scattered from the radiation source beam is detected by the strategically positioned detectors, thus improving image quality.

In a fully deployed configuration, the system is capable of scanning an OUI. An OUI could be any type of object, including cars, trucks, vans, cargo containers, mobile pallets with cargo, or any other type of cargo object. During the scanning process, the OUI remains in the area demarcated by the deployed boom (not shown) as a fixed piece of cargo while the self-contained inspection rig/tractor trailer 2700 moves over the OUI. Alternatively, the self-contained inspection rig/tractor trailer 2700 can remain in place while a piece of cargo is driven, moved, dragged, tagged, and/or lifted through the scanning region. As the self-contained inspection trailer 2700 is moved over OUI, an image of the OUI is produced on the inspection computers housed within the trailer showing the radiation-induced images of the articles and objects contained within the OUI (not shown). Therefore, in a preferred embodiment, the system is designed such that the self-contained inspection trailer moves over the stationary object (OUI).

Figure 27H:
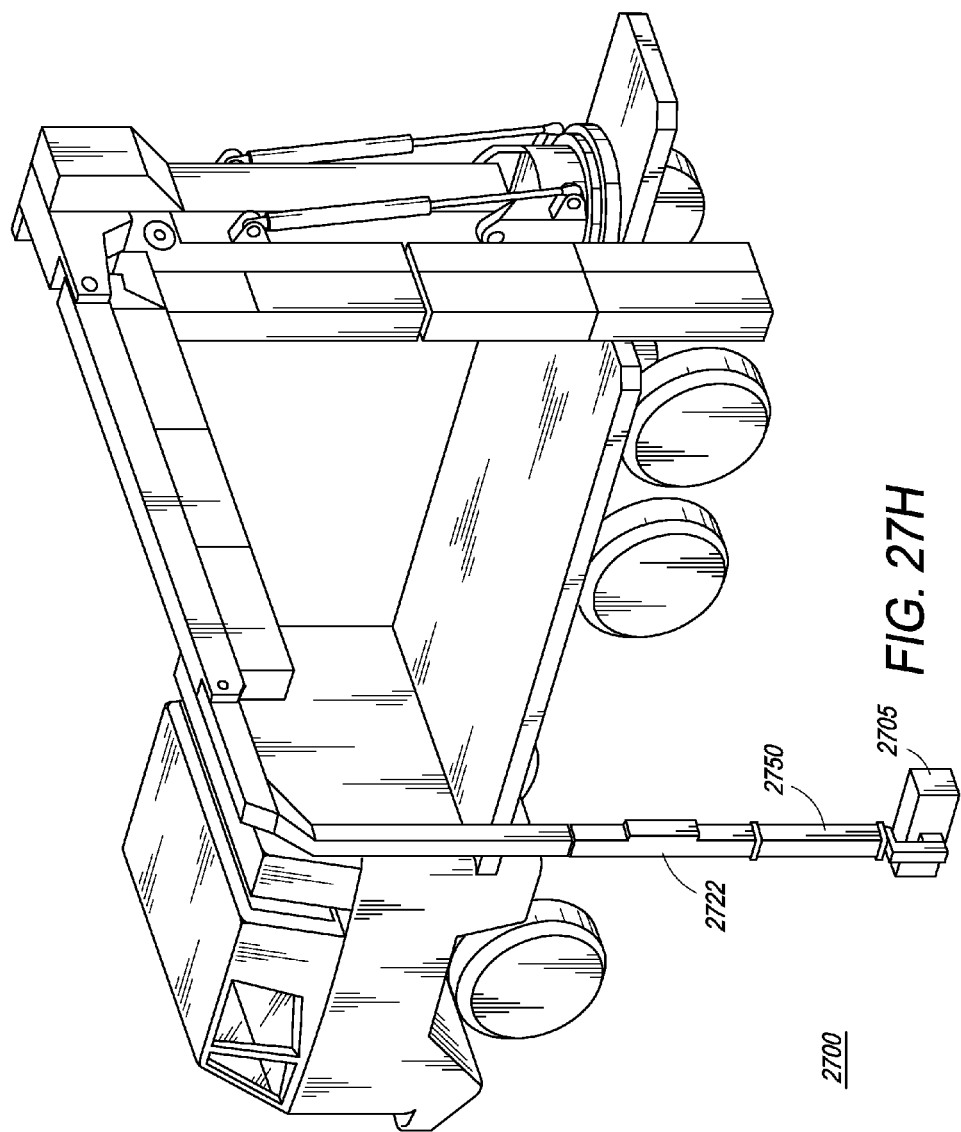
FIG. 27H is an illustration of one embodiment of a single boom system employed in the self-contained mobile inspection system of the present invention, in a fully deployed configuration, further illustrating the radiation source with height adjustment.

FIG. 27H is an illustration of one embodiment of a single boom system employed in the self-contained mobile inspection system of the present invention, in a fully deployed configuration, further illustrating a radiation source with height adjustment. As shown in FIG. 27H, radiation source box 2705 is attached to source arm 2722 using a telescopic arm 2750 that retracts into source arm 2722, in a vertical direction, depending upon the desired scanning height.

By forming system components, such as the detector array and the radiation source, so that they can fold into a stowed, storage configuration, it is possible to produce a compact trailer that can safely, and legally, travel roadways. A compact system is advantageous, in part, because it has a low center of gravity, thus allowing the system to be driven on unpaved roads, hilly terrain, and in off-road conditions. Further, the overall dimensions of the stowed system are small enough to allow for the mobile scanning system to be air-transported in a cargo plane for rapid deployment to remote areas. And finally, there is less operational space required for deployment.

The above examples are merely illustrative of the many applications of the system of present invention. Although only a few embodiments of the present invention have been described herein, it should be understood that the present invention might be embodied in many other specific forms without departing from the spirit or scope of the invention. For example, other configurations of cargo, tires, tankers, doors, airplane, packages, boxes, suitcases, cargo containers, automobile semi-trailers, tanker trucks, railroad cars, and other similar objects under inspection can also be considered. Therefore, the present examples and embodiments are to be considered as illustrative and not restrictive, and the invention is not to be limited to the details given herein, but may be modified within the scope of the appended claims.

We claim:

1. A foldable boom structure for use in a cargo inspection system wherein said foldable boom structure comprises a stowed configuration and an operational configuration:
   a. wherein the stowed configuration comprises
      a first section, having a first end and a second end, wherein said first section is in a first plane and is pivotally coupled, at the first end, to a back surface of a vehicle and wherein said first plane is substantially parallel to a plane defined by the back surface of the vehicle;
      a second section having a first end and a second end, wherein said second section is substantially parallel to the first section, and wherein the first end of the second section is pivotally connected to the second end of the first section; and
      a third section having a first end and a second end, wherein said third section is substantially parallel to the first section and the second section, and wherein the first end of the third section is pivotally connected to the second end of the second section; and
   b. wherein the operational configuration comprises
      said first section, in a second plane, wherein said second plane is substantially perpendicular to the plane defined by the back surface of the vehicle;
      said second section, wherein said second section is substantially perpendicular to the first section and wherein the first end of the second section is pivotally connected to the second end of the first section; and
      said third section, wherein said third section is substantially parallel to the first section and perpendicular to the second section and wherein the first end of the third section is pivotally connected to the second end of the second section.

2. The foldable boom structure of claim 1 further comprising a first detector array housing physically attached to the second section, wherein said first detector array housing contains a plurality of detectors.

3. The foldable boom structure of claim 2 further comprising a second detector array housing physically attached to the third section, wherein the second detector array housing contains a plurality of detectors.

4. The foldable boom structure of claim 3 wherein, in the operational configuration, said first detector array and said second detector array are arranged to receive transmitted radiation from at least one radiation source.

5. The foldable boom structure of claim 4 wherein the radiation source comprises at least one gamma ray source.

6. The foldable boom structure of claim 5 wherein the at least one gamma ray source is $^{60}Co$ or $^{137}Cs$.

7. The foldable boom structure of claim 1 wherein said foldable boom structure is adapted to be positioned to form a scan angle position relative to the vehicle and wherein the scan angle position ranges between 80° and 100°.

8. A foldable boom structure for use in a cargo inspection system wherein said foldable boom structure comprises a stowed configuration and an operational configuration:
   a. wherein the stowed configuration comprises
      a first linear member, having a first end and a second end, wherein said first section is substantially horizontal and is coupled, at the first end, to a back surface of a vehicle;
      a second linear member having a first end and a second end, wherein said second linear member is substantially horizontal, and wherein the first end of the second linear member is pivotally connected to the second end of the first linear member; and
      a third linear member having a first end and a second end, wherein said third linear member is substantially horizontal, and wherein the first end of the third linear member is pivotally connected to the second end of the second linear member; and
   b. wherein the operational configuration comprises
      said first linear member, wherein said first linear member is substantially vertical, wherein the second end is elevated relative to the first end, and wherein the first end is coupled to the back surface of a vehicle;
      said second linear member, wherein said second linear member is substantially horizontal, wherein said second linear member is perpendicular to the first linear member, and wherein the first end of the second linear member is pivotally connected to the second end of the first linear member; and
      said third linear member, wherein said third linear member is substantially parallel to the first linear member and perpendicular to the second linear member and wherein the first end of the third linear member is pivotally connected to the second end of the second linear member.

9. The foldable boom structure of claim 8 further comprising a detector array housing physically attached to the second linear member, wherein said detector array housing contains a plurality of detectors.

10. The foldable boom structure of claim 9 wherein, in the operational configuration, said plurality of detectors is arranged to receive transmitted radiation from at least one radiation source.

11. The foldable boom structure of claim 10 wherein the radiation source comprises at least one gamma ray source.

12. The foldable boom structure of claim 11 wherein the at least one gamma ray source is $^{60}Co$ or $^{137}Cs$.

13. The foldable boom structure of claim 8 further comprising a detector array housing physically attached to the third linear member, wherein the detector array housing contains a plurality of detectors.

14. The foldable boom structure of claim 13 wherein, in the operational configuration, said plurality of detectors is arranged to receive transmitted radiation from at least one radiation source.

15. The foldable boom structure of claim 14 wherein the radiation source comprises at least one gamma ray source.

16. The foldable boom structure of claim 15 wherein the at least one gamma ray source is $^{60}$Co or $^{137}$CS.

17. The foldable boom structure of claim 8 wherein said foldable boom structure is adapted to be positioned to form a scan angle position relative to the vehicle and wherein the scan angle position ranges between 80° and 100°.

18. The foldable boom structure of claim 8 further comprising a first detector array housing physically attached to the second section, wherein said first detector array housing contains a plurality of detectors.

19. The foldable boom structure of claim 18 further comprising a second detector array housing physically attached to the third section, wherein the second detector array housing contains a plurality of detectors.

20. The foldable boom structure of claim 19 wherein, in the operational configuration, at least one of said first detector array or said second detector array are arranged to receive transmitted radiation from at least one radiation source.

* * * * *